US009101124B2

(12) United States Patent (10) Patent No.: US 9,101,124 B2
Hill et al. (45) Date of Patent: Aug. 11, 2015

(54) COMPOSITE MATERIAL INCLUDING A THERMOPLASTIC POLYMER, A PEST FOOD MATERIAL AND A PESTICIDE

(75) Inventors: Robert L. Hill, Carmel, IN (US); James E. King, Carmel, IN (US); Joseph J. DeMark, Westfield, IN (US); Anton Arnoldy, Brownsburg, IN (US); Mike P. Tolley, Indianapolis, IN (US); Donald E. Williams, III, Greenfield, IN (US); Joseph E. Eger, Jr., Tampa, FL (US)

(73) Assignee: Dow AgroSciences LLC, Indianapolis, IN (US)

( * ) Notice: Subject to any disclaimer, the term of this patent is extended or adjusted under 35 U.S.C. 154(b) by 1778 days.

(21) Appl. No.: 12/004,655

(22) Filed: Dec. 21, 2007

(65) Prior Publication Data
US 2008/0187565 A1 Aug. 7, 2008

Related U.S. Application Data

(60) Provisional application No. 60/876,351, filed on Dec. 21, 2006.

(51) Int. Cl.
A01M 1/20 (2006.01)
A01M 1/02 (2006.01)
A01N 25/00 (2006.01)
A01N 47/34 (2006.01)

(52) U.S. Cl.
CPC ............ *A01M 1/2011* (2013.01); *A01M 1/026* (2013.01); *A01N 25/006* (2013.01); *A01N 47/34* (2013.01)

(58) Field of Classification Search
None
See application file for complete search history.

(56) References Cited

U.S. PATENT DOCUMENTS

| 2,590,211 | A | * | 3/1952 | Rugar ..................... 106/18.24 |
| 3,318,769 | A | | 5/1967 | Folckemer et al. |
| 3,564,750 | A | | 2/1971 | Burgess |
| 3,778,805 | A | | 12/1973 | Gould |
| 3,836,842 | A | | 9/1974 | Zimmermann et al. |
| 3,952,741 | A | | 4/1976 | Baker |

(Continued)

FOREIGN PATENT DOCUMENTS

| CA | 355888 | 2/1936 |
| EP | 0 283 142 A1 | 9/1988 |

(Continued)

OTHER PUBLICATIONS

Lingrey (Environmental Technologies, Inc, Part No. PX-00-0187, ©2003, p. 1-3, accessed via www.enviro-tec.com Jun. 13, 2011.).*

(Continued)

*Primary Examiner* — Bethany Barham
*Assistant Examiner* — Barbara Frazier
(74) *Attorney, Agent, or Firm* — Carl D. Corvin; Barnes & Thornburg LLP

(57) ABSTRACT

Composite materials that are palatable to a wood-destroying pest species and also pesticidal to the pest species can be used in pest control devices and can be used as wood substitutes for structural components, which are resistant to destruction by wood-destroying pests. The composite materials include a thermoplastic polymer, a food material for the pest and a pesticide. The composite material is formed by mixing a thermoplastic polymer, wood fragments or other cellulosic materials and a quantity of pesticide, and thereafter creating a molten material within a mixer, compounder, extruder or the like. The molten material is extruded or molded to form the desired shape.

1 Claim, 29 Drawing Sheets

(56) References Cited

U.S. PATENT DOCUMENTS

| | | |
|---|---|---|
| 4,074,456 A | 2/1978 | Tidwell |
| 4,105,971 A | 8/1978 | Nevalainen |
| 4,127,110 A | 11/1978 | Bullara |
| 4,136,338 A | 1/1979 | Antenore |
| 4,237,113 A | 12/1980 | Cardarelli |
| 4,265,252 A | 5/1981 | Chubbuck et al. |
| 4,366,644 A | 1/1983 | Lawrence |
| 4,387,529 A | 6/1983 | Hedstrom |
| 4,455,441 A | 6/1984 | Prestwich |
| 4,472,904 A | 9/1984 | Wasielewski |
| 4,631,231 A | 12/1986 | Stendel et al. |
| 4,653,221 A | 3/1987 | Pratscher |
| 4,688,026 A | 8/1987 | Scribner et al. |
| 4,737,770 A | 4/1988 | Brunius et al. |
| 4,737,789 A | 4/1988 | Nysen |
| 4,826,685 A | 5/1989 | Stewart |
| 4,843,752 A | 7/1989 | Munemasa et al. |
| 4,862,145 A | 8/1989 | Meehan et al. |
| 4,951,057 A | 8/1990 | Nagel |
| 4,961,283 A | 10/1990 | Forbes |
| 4,988,510 A | 1/1991 | Brenner et al. |
| 5,024,832 A | 6/1991 | Omata et al. |
| 5,042,194 A | 8/1991 | Cohen |
| 5,079,238 A | 1/1992 | Van Horn |
| 5,116,414 A | 5/1992 | Burton et al. |
| 5,134,892 A | 8/1992 | Wilson et al. |
| 5,209,233 A | 5/1993 | Holland et al. |
| 5,237,310 A | 8/1993 | Smith |
| 5,285,688 A | 2/1994 | Robbins et al. |
| 5,329,726 A | 7/1994 | Thorne et al. |
| 5,428,345 A | 6/1995 | Bruno |
| 5,429,735 A | 7/1995 | Johnson et al. |
| 5,528,222 A | 6/1996 | Moskowitz et al. |
| 5,564,222 A | 10/1996 | Brody |
| 5,571,967 A | 11/1996 | Tanaka et al. |
| 5,575,105 A | 11/1996 | Otomo |
| 5,592,774 A | 1/1997 | Galyon |
| 5,648,758 A | 7/1997 | Tweadey, II et al. |
| 5,661,651 A | 8/1997 | Geschke et al. |
| 5,739,514 A | 4/1998 | Uchida |
| 5,764,138 A | 6/1998 | Lowe |
| 5,801,194 A | 9/1998 | Van Voris et al. |
| 5,815,090 A | 9/1998 | Su |
| 5,864,241 A | 1/1999 | Schreck et al. |
| 5,876,577 A | 3/1999 | McAleer et al. |
| 5,877,422 A | 3/1999 | Otomo |
| 5,892,444 A | 4/1999 | Wittmer et al. |
| 5,894,818 A | 4/1999 | Betzen |
| 5,910,776 A | 6/1999 | Black |
| 5,937,571 A | 8/1999 | Megargle et al. |
| 5,950,356 A | 9/1999 | Nimocks |
| 5,974,344 A | 10/1999 | Shoemaker, II |
| 5,974,726 A | 11/1999 | Creeger et al. |
| 5,986,570 A | 11/1999 | Black et al. |
| 5,997,784 A | 12/1999 | Kamoski |
| 6,016,625 A | 1/2000 | Bishoff et al. |
| 6,025,725 A | 2/2000 | Gershenfeld et al. |
| 6,060,076 A | 5/2000 | Van Voris et al. |
| 6,099,850 A | 8/2000 | Van Voris et al. |
| 6,100,805 A | 8/2000 | Lake |
| 6,111,520 A | 8/2000 | Allen et al. |
| 6,130,602 A | 10/2000 | O'Toole |
| 6,150,944 A | 11/2000 | Martin et al. |
| 6,178,834 B1 | 1/2001 | Cates |
| 6,243,014 B1 | 6/2001 | Lake et al. |
| 6,255,959 B1 | 7/2001 | Lake et al. |
| 6,281,799 B1 | 8/2001 | Lake et al. |
| 6,304,185 B1 | 10/2001 | Tuttle et al. |
| 6,313,748 B1 | 11/2001 | Lake |
| 6,319,511 B1 | 11/2001 | Van Voris et al. |
| 6,337,079 B1 | 1/2002 | Maindron |
| 6,339,897 B1 | 1/2002 | Hayes et al. |
| 6,370,812 B1 | 4/2002 | Burns et al. |
| 6,397,516 B1 | 6/2002 | Su |
| 6,404,210 B1 | 6/2002 | Su |
| 6,416,752 B1 | 7/2002 | Richardson et al. |
| 6,478,440 B1 | 11/2002 | Jawordki et al. |
| 6,515,591 B2 | 2/2003 | Lake et al. |
| 6,615,535 B2 | 9/2003 | Snell et al. |
| 6,630,887 B2 | 10/2003 | Lake |
| 6,668,483 B1 | 12/2003 | Trivisani et al. |
| 6,724,312 B1 | 4/2004 | Barber et al. |
| 6,803,051 B1 | 10/2004 | Van Voris et al. |
| 6,852,328 B1 | 2/2005 | Van Voris et al. |
| 6,881,367 B1 | 4/2005 | Baker |
| 6,914,529 B2 | 7/2005 | Barber et al. |
| 6,937,156 B2 | 8/2005 | Gardner, Jr. et al. |
| 7,163,974 B2 | 1/2007 | Manning et al. |
| 7,212,112 B2 | 5/2007 | Barber et |
| 7,212,129 B2 | 5/2007 | Barber et |
| 7,262,702 B2 | 8/2007 | Barber et al. |
| 7,335,374 B2 | 2/2008 | Van Voris et al. |
| 7,348,890 B2 | 3/2008 | Barber et al. |
| 2001/0001236 A1 | 5/2001 | Lake |
| 2001/0004237 A1 | 6/2001 | Lake et al. |
| 2001/0009399 A1 | 7/2001 | Barber et al. |
| 2001/0033230 A1 | 10/2001 | Barber et al. |
| 2001/0054962 A1 | 12/2001 | Barber et al. |
| 2002/0192259 A1 | 12/2002 | Van Voris et al. |
| 2003/0029076 A1 | 2/2003 | Snell et al. |
| 2003/0049293 A1 | 3/2003 | Jobic |
| 2003/0071389 A1 | 4/2003 | Manning et al. |
| 2003/0152605 A1 | 8/2003 | Martin et al. |
| 2003/0160699 A1 | 8/2003 | Trompen |
| 2003/0177689 A1* | 9/2003 | Su .................................. 43/131 |
| 2003/0184442 A1 | 10/2003 | Gardner, Jr. et al. |
| 2005/0091911 A1 | 5/2005 | Matts et al. |
| 2005/0233138 A1 | 10/2005 | Jobic |
| 2006/0201053 A1 | 9/2006 | Van Voris et al. |
| 2007/0044372 A1 | 3/2007 | Lang et al. |
| 2007/0120690 A1 | 5/2007 | Barber et al. |
| 2008/0055094 A1 | 3/2008 | Barber et al. |
| 2009/0023667 A1 | 1/2009 | Tomura et al. |

FOREIGN PATENT DOCUMENTS

| | | |
|---|---|---|
| GB | 117916 | 6/1917 |
| GB | 590826 | 7/1947 |
| GB | 1040553 | 9/1966 |
| GB | 1513190 | 6/1978 |
| JP | 7-43460 | 2/1995 |
| JP | 9-26320 | 1/1997 |
| JP | 9-98701 | 4/1997 |
| JP | 10-56935 | 3/1998 |
| JP | 10-84834 | 4/1998 |
| JP | 10-105861 | 4/1998 |
| JP | 11-239440 | 9/1999 |
| JP | 2006296432 | 11/2006 |
| WO | WO 85/04074 | 9/1985 |
| WO | WO 93/23998 | 12/1993 |
| WO | WO 98/21961 | 5/1998 |
| WO | WO 98/46071 | 10/1998 |
| WO | WO 99/41983 | 8/1999 |
| WO | WO 00/79243 | 12/2000 |
| WO | WO 01/06851 A1 | 2/2001 |
| WO | WO 02/26033 A1 | 4/2002 |
| WO | WO 02/043487 | 6/2002 |
| WO | WO 03/013237 A2 | 2/2003 |
| WO | WO 03/067977 | 8/2003 |
| WO | WO 03/079779 A1 | 10/2003 |
| WO | WO 03/082002 | 10/2003 |
| WO | 2005079572 | 9/2005 |
| WO | 2005094578 | 10/2005 |
| WO | WO 2005/092029 | 10/2005 |
| WO | WO 2007/014344 | 2/2007 |
| WO | WO 2008/082541 | 7/2008 |
| ZA | 847774 | 10/1984 |

OTHER PUBLICATIONS

Malm et al. ("Properties of cellulose esters of acetic, propionic, and butyric acids", Ind. Eng. Chem. 1942, 34(4) p. 430-435).*

(56) References Cited

OTHER PUBLICATIONS

Hexaflumuron MSDS accessed via PPDB http://sitem.herts.ac.uk/aeru/iupac/Reports/383.htm on May 16, 2012, p. 1-7, last updated Dec. 22, 2011.*

Noviflumuron MSDS accessed via PPDB http://sitem.herts.ac.uk/aeru/iupac/Reports/1355.htm on May 16, 2012, p. 1-6, last updated Aug. 6, 2011.*

Patent Cooperation Treaty International Search Report. PCT Patent Application No. PCT/US2007/026265. May 6, 2008.

Patent Cooperation Treaty Written Opinion of the International Searching Authority. PCT Patent Application No. PCT/US2007/026265. May 6, 2008.

Amendment Under PCT Article 34. PCT Patent Application No. PCT/US2007/026265. Oct. 15, 2008.

Remarks in Response to Written Opinion of the International Searching Authority Mailed May 6, 2008. PCT Patent Application No. PCT/US2007/026265. Oct. 15, 2008.

Patent Cooperation Treaty International Preliminary Report on Patentability. PCT Patent Application No. PCT/US2007/026265. Mar. 27, 2009.

XP-002167431, Miyauchi Shin'nosuke, Ohmiya Yukio, Yokotsuka Masatoshi, Ohkita Kumakazu, "Electrical Properties of Carbon Black-Graftpolymers Crosslinked with Peroxide-Divinyl Monomer System," vol. 25, J Soc Mater Sci Jpn, Oct. 1976. (Abstract only).

"Charge Transfer Sensing" by Hal Philipp; Copyright ©1997.

Sentricon Colony Elimination System; Dow AgroSciences; Mar. 26, 1999.

Passive RFID Device with Sensor Input; MCRF202; Microchip Technology Inc.; Copyright ©1999.

DS2405 Addressable Switch, Dallas Semiconductor, Jul. 2002.

Disclosed Anonymously. Extruded Thermoplastic and Cellulose Materials Acceptable to Termintes as Monitors or Bait. Prior Art Database, www.ip.com, May 3, 2005.

SciFinder Search Report; Sep. 14, 2003.

Declaration of Philip J. Howard and exhibits, executed Mar. 17, 2015, 54 pages.

Declaration of Joe K. Mauldin and exhibit, executed Mar. 10, 2015, 9 pages.

* cited by examiner

R. virginicus Extruded Noviflumuron Survivorship at 8 Weeks - No Choice

Treatments with the same letter are not significantly different Binary Logistic Regression, $p \geq 0.05$ R. flavipes Extruded Spinosad & Fipronil Survivorship at 14-D - Choice vs SYP Treatments with the same letter are not significantly different Binary Logistic Regression, $p \geq 0.05$

COMPOSITE MATERIAL INCLUDING A THERMOPLASTIC POLYMER, A PEST FOOD MATERIAL AND A PESTICIDE

CROSS-REFERENCE TO RELATED APPLICATION

The present application claims the benefit of U.S. Provisional Patent Application No. 60/876,351 filed 21 Dec. 2006, which is incorporated herein by reference in its entirety.

BACKGROUND

The present application relates to composite materials that are palatable to a wood-destroying pest species and also pesticidal to the pest species. More particularly, but not exclusively, the application relates to composite materials composed of a thermoplastic polymer, a food material for the pest and a pesticide.

The protection of wooden structures from damage caused by pests has been an area of particular interest for many years, and the removal of pests from areas occupied by humans, livestock, and crops has long been a challenge. Pests of frequent concern include various types of insects and rodents. Subterranean termites are a particularly troublesome type of pest with the potential to cause severe damage to wooden structures. Various schemes have been proposed to eliminate termites and certain other harmful pests of both the insect and noninsect variety. In one approach, pest control relies on the blanket application of chemical pesticides in the area to be protected. However, as a result of environmental regulations, this approach is becoming less desirable.

Recently, advances have been made to provide for the targeted delivery of pesticide chemicals. U.S. Pat. No. 5,815,090 to Su is one example. Another example directed to termite control is the SENTRICON® Termite Colony Elimination System of Dow AgroSciences LLC that has a business address of 9330 Zionsville Road, Indianapolis, Ind. In this system, a number of units each having a termite edible material, are placed at least partially in the ground about a dwelling to be protected. The units are inspected routinely by a pest control service for the presence of termites, and inspection data is recorded with reference to a unique barcode label associated with each unit. If termites are found in a given unit, a bait is installed that contains a slow-acting pesticide intended to be carried back to the termite nest to eradicate the colony.

There is a continuing demand for further advancement in the areas of pest control, pest-resistant structural materials and related technologies, and the development of new techniques for more reliably and/or cost-effectively preventing damage to wooden structures and eradicating termites or other pests are desired.

SUMMARY

In one aspect, the present application provides a pest control device that includes a bait operable to be consumed or displaced by one or more species of pest and a housing at least partially enclosing the bait. The bait includes a composite material including a plastic structural matrix, a cellulosic food material contained within the matrix that is palatable to the pest and a pesticide contained within the matrix that is toxic to the pest.

In another aspect, the application provides a pest control system that includes at least two pest control devices each arranged to be spaced apart from one another in an area to be protected from one or more pests. At least one of the pest control devices includes a bait that is operable to be consumed or displaced by the pest and that includes a composite material including a plastic structural matrix, a cellulosic food material contained within the matrix that is palatable to the pest and a pesticide contained within the matrix that is toxic to the pest.

In yet another aspect, the application provides a method that includes: (1) providing a pest control device including a pesticidal bait for one or more species of pest; and (2) installing the device in an area to be protected from the pests. The pesticidal bait includes a composite material including a plastic structural matrix, a cellulosic food material contained within the matrix that is palatable to the pest and a pesticide contained within the matrix that is toxic to the pest.

In still another aspect, the application provides a method for making a composite material that includes: (1) providing a mixture of a softened or molten thermoplastic polymer having a softening or melting point below about 220° C., a cellulosic food material that is palatable to at least one species of wood-destroying pest and a pesticide that is toxic to the pest; (2) forming the mixture to provide a workpiece having a desired shape; and (3) cooling the workpiece to a temperature below the softening or melting point of the plastic to provide a solid composite article. As used herein, the term "molten" is intended to refer to a state of a thermoplastic polymer in which the polymer is fully melted, partially melted, or sufficiently softened or tacky that the polymer can be formed, for example by extrusion or molding and then cooling, into a plastic matrix. Similarly, the term "melting point" as used herein is intended to refer to the temperature at which a given polymer or mixture of polymers melts, softens or becomes tacky, and encompasses the glass transition temperature for amorphous polymers. A person skilled in the art will appreciate that the melting point of a given polymer or mixture of polymers can be modified by contacting the polymer or mixture of polymers with certain solvents and/or other additives. In one embodiment, the mixture is formed by extrusion.

In another aspect of the present application, there is provided a composite material that includes a plastic structural matrix, a cellulosic food material contained within the matrix that is palatable to at least one species of wood-destroying pest and a pesticide contained within the matrix that is toxic to the pest. The composite material is operable to be consumed or displaced by the pest; and the plastic structural matrix comprises a thermoplastic polymer having a melting point below about 220° C.

Also provided by the present application is a composite material that includes a plastic structural matrix, a cellulosic food material contained within the matrix that is palatable to at least one species of wood-destroying pest and a pesticide contained within the matrix that is toxic to the pest; in which the composite material is operable to be consumed or displaced by the pest, and the plastic structural matrix comprises a thermoplastic polymer that includes a thermoplastic cellulose derivative.

In yet another aspect of the present application, there is provided a composite material that includes a rigid plastic structural matrix comprising a thermoplastic polymer, a cellulosic food material contained within the matrix that is palatable to at least one species of wood-destroying pest and a pesticide contained within the matrix that is toxic to the pest, in which the composite material is operable to be consumed or displaced by the pest.

In still another aspect of the application, there is provided an extruded wood substitute material that includes a composite material including a plastic structural matrix, a cellulosic food material contained within the matrix that is palatable to the pest and a pesticide contained within the matrix that is toxic to the pest.

Further embodiments, forms, features and aspects of the present application shall become apparent from the detailed description and figures provided herewith.

DETAILED DESCRIPTION OF SELECTED EMBODIMENTS

Figure 1:
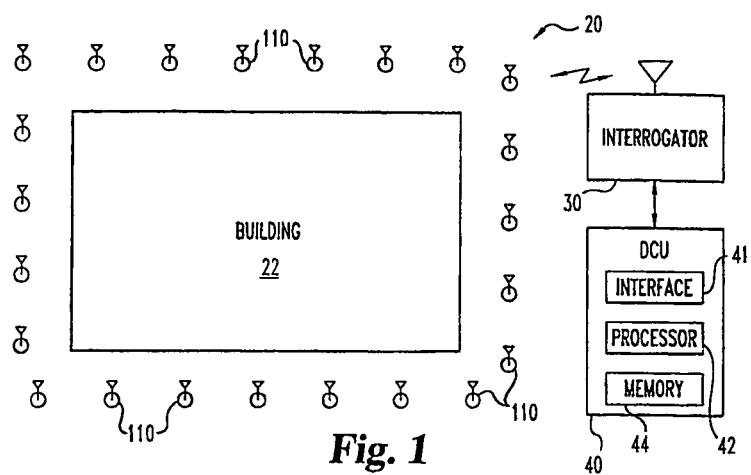
FIG. 1 is a diagrammatic view of a pest control system that includes several pest control device.

For the purposes of promoting an understanding of the principles of the inventions described herein, reference will now be made to the embodiments illustrated in the drawings and specific language will be used to describe the same. It will nevertheless be understood that no limitation of the scope of any invention is thereby intended. Any alterations and further modifications in the illustrated embodiments, and any further applications of the principles described and illustrated herein are contemplated as would normally occur to one skilled in the art.

Composite materials that can be used to deliver pesticides to wood-destroying pests include a plastic structural matrix, a cellulosic food material palatable to at least one species of wood-destroying pest and a pesticide that is toxic to the pest. The term "wood-destroying pest" is used herein to refer to an insect or other pest that destroys the structural integrity of wood by boring into wood or consuming wood. Examples include, without limitation, termites, carpenter ants, carpenter wasps and other wood boring or cellulose consuming organisms. Making the composite materials described herein does not require material processing at high temperatures that would destroy the functionality of the pesticide. The term "pesticide" is used herein to refer to a compound that is toxic to at least one target species of wood-destroying pests. The plastic structural matrix of the composite is composed of a thermoplastic polymer processed into a form that provides sufficient strength and structural integrity for a desired end use of the composite material. The pesticide retains its bioactivity as it resides within the composite, and produces a desired result after the material is ingested by or otherwise comes into contact with pests. Polymeric materials included in the composite materials can be processed using relatively low-temperature extrusion or molding processes and provide composite material articles with structural integrity, with good acceptance by target wood-destroying pests (i.e., palatability to target wood-destroying pests), and without nullifying the functionality of pesticides processed therewith, which can include temperature sensitive pesticides. In one embodiment, the plastic structural matrix of the composite material is rigid.

In one embodiment, the cellulosic food material is selected based upon known or measured attractability for a given pest that is being targeted. For example, when a composite material is to be used as a bait for a certain target pest species, the composite material can be made using a cellulosic food material that is a favorite food of the target pest species. The cellulosic food material would therefore attract members of the target pest species and would be expected to be consumed or displaced by the pests, which would result in the simultaneous consumption or displacement of the pesticide present in the composite material, producing a desired pesticidal effect. The food material can be composed in whole or in part by an edible plastic material. Alternatively, the food material can be composed in whole or in part by a non-plastic cellulosic material. In one embodiment, the food material is a purified cellulose, such as, for example, alpha cellulose, beta cellulose or gamma cellulose. One suitable example is preferred texture cellulose (PTC). In another embodiment, the food material is wood or a derivative of wood, such as, for example, wood chips, wood fibers, sawdust, cardboard, paper or other material that is palatable to a target wood-destroying species. Other cellulosic food materials that can be employed include microcrystalline cellulose, examples of which are provided in U.S. Pat. No. 6,416,752, which is incorporated herein by reference, and modified polymeric cellulose based materials such as, for example, METHOCEL® or ETHOCEL®, which are available commercially from The Dow Chemical Company, Midland, Mich.

The pesticide is one that is effective to kill pests that ingest or contact the pesticide. Some of the pesticides that can be employed in a composite material as disclosed herein include, but are not limited to the following:

1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha cypermethrin, alpha ecdysone, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate, barium hexafluorosilicate, barthrin, benclothiaz, bendiocarb, benfuracarb, benomyl, benoxafos, bensuliap, benzoximate, benzyl benzoate, beta cyfluthrin, beta cypermethrin, bifenazate, bifenthrin, binapacryl, bioallethrin, bioethanomethrin, biopermethrin, bistrifluron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuform, chloromethiuron, chloropicrin, chloropropylate, chlorphoxim, chlorprazophos, chlorpyrifos, chlorpyrifos methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A &B, crufomate, cryolite, cyanofenphos, cyanophos, cyanthoate, cyclethrin, cycloprothrin, cyenopyrafen, cyflumetofen, cyfluthrin, cyhalothrin, cyhexatin, cypermethrin, cyphenothrin, cyromazine, cythioate, d-limonene, dazomet, DBCP, DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfiram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma cyhalothrin, gamma HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, ometh oate, oxamyl, oxydemeton methyl, oxydeprofos, oxydisulfoton, paradichlorobenzene, parathion, parathion methyl, penfluron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfiram, sulfluramid, sulfotep, sulfur, sulfuryl fluoride, sulprofos, tau fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidothion, vamidothion, vaniliprole, vaniliprole, XMC, xylylcarb, zeta cypermethrin and zolaprofos.

Additionally, any combination of the above pesticides can be used.

For more information consult "Compendium of Pesticide Common Names" located at http://www.alanwood.net/pesticides/index.html as of the filing date of this document. Also consult "The Pesticide Manual" 14th Edition, edited by C D S Tomlin, copyright 2006 by British Crop Production Council.

In one embodiment, the pesticide is one that has an immediate effect upon ingestion by or contact with a pest (referred to herein as an "immediate action" pesticide or a "fast acting" pesticide). For example, insecticides that have immediate killing action upon ingestion by termites include chlorpyrifos, spinosad, imidacloprid and fipronil, each of which is well known and available commercially. As used herein, the term "immediate" is intended to mean that the pesticide typically operates to kill an individual pest before the pest returns to its colony. In another embodiment, the pesticide is one that exhibits a delayed effect upon ingestion by or contact with a pest (referred to herein as a "delayed action" pesticide). For example, insecticides that have delayed killing activity upon ingestion by or contact with termites include hexaflumuron and noviflumuron, each of which is well known and available commercially. As used herein, the term "delayed" is intended to mean that the pesticide typically does not operate to kill an individual pest until after the pest has returned to its colony. In another embodiment, the pesticide is selected from the group consisting of lufenuron, diflubenzuron, flufenoxuron and hydramethylnon.

The plastic structural matrix in one embodiment comprises a polymer that has a melting point of below about 220° C. In another embodiment, the plastic structural matrix comprises a polymer that has a melting point of below about 200° C. In yet another embodiment, the plastic structural matrix comprises a polymer that has a melting point of no greater than about 180° C. The plastic structural matrix in another embodiment comprises a polymer that has a melting point of below about 160° C. In still yet another embodiment, the plastic structural matrix comprises a polymer that has a melting point of below about 140° C. The processing temperature used to melt the polymer when making the composite material is a temperature less than that at which the functionality of the pesticide is nullified. In another embodiment, the thermoplastic polymer included in the composite material is one that is palatable to the target pest species (also referred to herein as a "pest-edible polymer"). In yet another embodiment, the plastic structural matrix comprises a thermoplastic cellulose derivative. In one preferred embodiment, the matrix includes a cellulose acetate. For example, the cellulose acetate in one embodiment is one with a degree of polymerization of from about 50 to about 400 monomer units. In another embodiment, the polymer includes cellulose acetate butyrate. For example, the cellulose acetate butyrate in one embodiment is one with a degree of polymerization of from about 50 to about 400 units. In another embodiment, the cellulose acetate butyrate has a degree of polymerization of from about 100 to about 300 units. In yet another embodiment, a cellulose acetate butyrate included in the composite has about 160 units. In yet another embodiment, the matrix includes cellulose acetate propionate. For example, the cellulose acetate propionate in one embodiment is one with a degree of polymerization of from about 50 to about 400 units. In another embodiment, the cellulose acetate propionate has a degree of polymerization of from about 100 to about 300. Alternatively, a wide variety of other polymers can be utilized.

The application also contemplates that the thermoplastic polymer can include a single polymer or a mixture of at least two different polymers. For example, in one embodiment, the thermoplastic polymer includes a mixture of a relatively high molecular weight polymer and a relatively low molecular weight polymer. One embodiment, for example, includes a mixture of a cellulose acetate butyrate having from about 50 to about 75 monomer units and a cellulose acetate butyrate having from about 150 to about 300 monomer units. Another embodiment includes a mixture of a cellulose acetate butyrate having about 60 monomer units and a cellulose acetate butyrate having about 300 monomer units. Yet another embodiment includes a mixture of a cellulose acetate butyrate having about 64 monomer units and a cellulose acetate butyrate having about 160 monomer units. In another embodiment, the thermoplastic polymer includes a mixture of a cellulose acetate propionate having from about 50 to about 75 monomer units and a cellulose acetate propionate having from about 150 to about 300 monomer units. Another embodiment includes a mixture of a cellulose acetate propionate having about 60 monomer units and a cellulose acetate propionate having about 300 monomer units. Yet another embodiment includes a mixture of a cellulose acetate propionate having about 64 monomer units and a cellulose acetate propionate having about 160 monomer units. The application contemplates a variety of additional combinations, as would occur to a person of ordinary skill in the art. In addition to mixtures that include polymers of different molecular weights, the application contemplates embodiments in which the thermoplastic polymer includes a mixture of different types of polymers. For example, the polymer can include a mixture of two or more of cellulose acetate, cellulose acetate butyrate and cellulose acetate propionate. Alternatively, the polymer can include a mixture of one or more of these with one or more other thermoplastic polymers or two or more other thermoplastic polymers. The mixture chosen has physical properties (i.e., processability features and palatability to wood-destroying pests) that are suitable for the uses described herein.

In addition to the polymer, the food material and the pesticide, other ingredients can optionally be included in the composite material. For example, some ingredients can be included to increase the stability or shelf life of the pesticide included in the composite. Other ingredients can be selected to improve the processability of the mixture, or to provide an advantageous effect after the composite material is formed. Still other ingredients can be selected, for example, to attract pests to the baits or to stimulate feeding. The composite materials disclosed herein can also include or be used with herbicides and fungicides, both for reasons of economy and synergy. The composite materials disclosed herein can also include or be used with antimicrobials, bactericides, defoliants, safeners, synergists, algaecides, attractants, desiccants, pheromones, repellants, animal dips, avicides, disinfectants, semiochemicals, and molluscicides (these categories not necessarily mutually exclusive) for reasons of economy, and synergy.

The composite material can be fabricated by way of a process that utilizes a combination of compounding and extrusions or molding to form articles composed of the composite material. The present application is not intended to be limited to the manufacture of articles having a specific shape, or "macrostructure." Rather, a wide variety of shapes are envisioned. Articles made in accordance with the application can be formed into a wide variety of shapes by extrusion, by post-extrusion processing, by original mold design, by post-molding processing or by a combination thereof.

To make a composite material in accordance with one embodiment, a mixture of a granular or particulate thermoplastic polymer, a pesticide and a cellulosic material is provided and the mixture is then compounded to mix the components, and extruded or molded at a predetermined temperature and pressure. The polymer, the cellulosic material and the pesticide can be combined using standard mixing or compounding techniques to mix the components and drive off excess moisture. For example, the materials can be mixed in a rotational mixer or compounding extruder. Heat is applied if needed to bring the mixture to a temperature at least as high has the melting point or glass transition temperature of the polymer (i.e., a temperature suitable to soften the amorphous portion of the polymer) but not to a temperature at which the functionality of the pesticide is nullified. The thermoplastic polymer softens upon reaching its melting point or glass transition temperature, making it pliable or plastic and therefore suitable for shaping, such as by extrusion. Preferably, the temperature is at least as high as the melting point of the polymer, but not so high that pesticide functionality is nullified. In one embodiment, the processing temperature is no greater than about 220° C., such as, for example, from about 90° C. to about 220° C. In another embodiment, the processing temperature is from about 170° C. to about 220° C. In another embodiment, the processing temperature is no greater than about 200° C., such as, for example, from about 90° C. to about 200° C. In another embodiment, the processing temperature is from about 150° C. to about 200° C. In another embodiment, the processing temperature is no greater than about 180° C., such as, for example, from about 90° C. to about 180° C. In another embodiment, the processing temperature is from about 130° C. to about 180° C. In another embodiment, the processing temperature is no greater than about 160° C., such as, for example, from about 90° C. to about 160° C. In another embodiment, the processing temperature is from about 110° C. to about 160° C. In another embodiment, the processing temperature is no greater than about 140° C., such as, for example, from about 90° C. to about 140° C. In another embodiment, the processing temperature is from about 100° C. to about 140° C. One skilled in the art will recognize that higher temperatures may be needed, and that the processing temperature may be optimized to allow the polymer to be processed as long as the temperature is not raised to a point that results in substantial harm to other components of the composite, such as, for example, charring the cellulosic food material or nullifying the functionality of the pesticide. A person of ordinary skill in the art will also understand that the inclusion of a solvent in the mixture can modify the softening temperature of the thermoplastic polymer material. In embodiments in which a solvent is present, it is understood that softening at the surface of a polymer, as modified by the solvent, might begin at a temperature that is lower than the natural melting point of the polymer in the absence of the solvent. In other words, temperatures below the natural melting point of the polymer may be suitable molding temperatures in embodiments in which the solvent is effective to soften the surface of the polymer at a temperature below its natural melting point.

A wide variety of extrusion or molding techniques can be used, many examples of which are known in the art. While it is not intended that the present application be limited by any theory, it is believed that, under extrusion or molding conditions applied in methods described herein, the polymer granules become softened, tacky or fully melted. When this occurs, pressure exerted upon the mixture causes softened polymer granules to contact one another and adhere together or causes the polymer to fully melt, whereby the molten polymer forms a continuous phase in the mixture. The temperature at which the compression is applied is a temperature less than that which would damage or denature the pesticide but high enough to achieve a desired level of polymer particle adhesion or polymer melting. It is understood that a wide variety of material specifications (such as polymer type, polymer size, granule size distribution and ratio of ingredients) and also a wide variety of process parameters (such as temperature and pressure) can be used to provide articles having various advantageous characteristics. It is within the ability of a skilled artisan, armed with the description of the present application, to select, without undue experimentation, advantageous combinations of materials and parameters to provide articles having differing levels of pesticide, different degrees of palatability to various wood-destroying pests, and different physical properties.

As will be appreciated by a person skilled in the art upon consideration of the descriptions herein, one aspect of the present application is a method for making a composite material that includes: (1) providing a mixture of a softened or molten thermoplastic polymer having a softening or melting point below about 220° C., a cellulosic food material that is palatable to at least one species of wood-destroying pest and a pesticide that is toxic to the pest; (2) forming the mixture to provide a workpiece having a desired shape; and (3) cooling the workpiece to a temperature below the softening or melting point of the plastic to provide a solid composite article. The heated mixture can optionally also include a plasticizer. In one embodiment, the quantity of plasticizer is at least about 1% by weight relative to the total weight of the mixture. In another embodiment, the quantity of plasticizer is at least about 1.5% by weight relative to the total weight of the mixture. In yet another embodiment, the quantity of plasticizer is from about 1% to about 5% by weight relative to the total weight of the mixture. In still another embodiment, the quantity of plasticizer is at least about 4.2% by weight relative to the total weight of the mixture. In one identified formulation, the polymer in the mixture is a cellulose acetate polymer and the plasticizer is a plasticizer for cellulose acetate. For example and without limitation, the plasticizer can be an ester of polyol and/or an ester of a hydroxyl carboxylic acid. Examples of suitable plasticizers include glycerol triacetate, triethylene glycol diacetate, an ester of citric acid and an ester of phthalic acid. Other suitable plasticizers include mixtures of adipate plasticizers such as, for example, diisobutyl adipate and dioctyl adipate at similar total concentrations of 1% to 5% of the extrusion matrix. In one embodiment, the diisobutyl adipate and dioctyl adipate are present in the mixture in a ratio of about 3:1 wt/wt.

In one manner of practicing the method, the molten mixture is provided by mixing the polymer, the food material and the pesticide to form a mixture and then compounding said mixture under elevated pressure and temperature to form a molten material. In another manner of practicing the method, the method includes forming pellets or flakes of the mixture prior to compounding. In one manner of making the composite material articles, all of the components are mixed together and then the mixture is heated above the melting point of the thermoplastic polymer included therein, e.g. up to about 220° C. in some embodiments, in a device, such as a twin screw mixer, that is capable of additional mixing followed by extrusion through a die, which imparts a specific cross-sectional profile to the composite material, and then cooling in a water bath or spray. In another manner of forming articles composed of the composite material, the polymers, cellulosic food materials and pesticides are combined within an extruder under positive pressure and at elevated temperature and are thereafter extruded to provide an elongated workpiece. Thereafter, cooling water is applied to the workpiece. The cooling can be achieved, for example, by applying a water bath to the workpiece or by spraying the workpiece with water.

The thermoplastic polymer levels in the mixture in one embodiment are from about 5% to about 50% of the total composite weight, with the remainder of the mixture comprising a cellulosic material (about 50% to about 85%), a pesticide (from about 0.001% to about 5%) and, optionally, lubricants (e.g., up to about 5%) and/or other processing additives which are used to help improve the processability of the mixture or the properties of the product. In another embodiment, the mixture includes from about 10% to about 40% polymer, from about 60% to about 85% cellulosic material and from about 0.001% to about 5% pesticide. In yet another embodiment, the mixture includes from about 15% to about 30% polymer, from about 70% to about 85% cellulosic material and from about 0.001% to about 5% pesticide. In other embodiments, the pesticide is present in an amount in the range of from about 0.4% to about 5%.

In another manner of practicing the method, the food material, such as, for example, purified alpha cellulose, is first pre-loaded with the pesticide (also referred to herein as "active ingredient" or "AI"). In one manner of pre-loading, the pesticide is sprayed directly on cellulose particles, and the mixture of cellulose particles and pesticide is then compacted and broken into prills, which include the cellulose food material and the pesticide therein. When this approach is used, the pesticide is referred to as "incorporated in cellulose," and this method is referred to as an "incorporated in cellulose" method. In another manner of pre-loading the food material with an AI, pre-formed prills of cellulose (which are available commercially, and can be obtained from International Fibers) are sprayed with the pesticide to provide a pre-loaded cellulose material. When this approach is used, the pesticide is referred to as "sprayed on cellulose," and this method is referred to as a "sprayed on cellulose" method. The cellulose/pesticide prills (or optionally the uncompacted cellulose/pesticide mixture) is mixed with the thermoplastic polymer material, and this mixture is then extruded at a temperature above the melting point of the thermoplastic polymer material. In one embodiment, the thermoplastic polymer material includes cellulose acetate butyrate. For example, the cellulose acetate butyrate can include a mixture of a cellulose acetate butyrate having a molecular weight of about 16,000 and a cellulose acetate butyrate having a molecular weight of about 40,000. When this mixture is used, it can be extruded at a temperature of 140° C. to 150° C. A lubricant can also be included to aide the flow of the matrix through an extrusion die. In one embodiment, the lubricant is calcium stearate.

In another manner of practicing the method cellulose prills are first compounded (for example, in a Gelimat compounder) with the thermoplastic polymer to provide cellulose/plastic prills, and then the pesticide is spray applied to the post-compounded cellulose/plastic prills. Calcium stearate can optionally be mixed with the post-compounded batch prior to spraying the pesticide onto the material. After the pesticide is applied, the mixture is extruded or otherwise molded. In experimental work using cellulose acetate butyrate (CAB), discussed further in the Examples below, a Gelimat compounder is used to blend and partially melt the CAB with other solid components through the use of intense shear and the generation of heat. In the Gelimat compounder, a 1000 HP motor drives a mixing paddle in a chamber having about a 1-cubic-foot volume, which contains the solids to be compounded. This mixing step distributes the CAB and also drives off water, which is deleterious in the extrusion process.

In another manner of practicing the method, the method includes: (a) adding the food material and the pesticide to an extruder mixing container; (b) contacting a hot thermoplastic polymer with the food material and pesticide to produce a food material/pesticide/thermoplastic polymer mixture; and (c) contacting the food material/pesticide/thermoplastic polymer mixture with a die to provide shape to the food material/pesticide/thermoplastic polymer mixture and to produce the workpiece. In one embodiment, the food material includes wood fibers.

In an alternate embodiment, a mixture of particulate polymer, cellulosic food material and pesticide, and optionally other ingredients, is formed into a composite material by injection molding. Alternatively or in addition, the mixture can be combined and pressed in a Carver press or other compression molding device. The composite material when injection into a mold cavity at a positive pressure and an elevated temperature takes the form of the mold and upon cooling produces a composite material as described above.

A composite material as provided herein can be used as a monitor or bait for a pest control device. In one example, the composite material can be used as a stand-alone bait for attracting and terminating pests as a single-step pesticide delivery tool without the need for monitoring by pest control professionals to determine whether such pests are present in a given area. Alternatively, it can be used with monitoring steps for determining the presence or absence of wood destroying pests. For example, it can be used as a replacement monitor or a bait in an already existing termite bait station such as, for example, the SENTRICON® Termite Colony Elimination bait station, as described further below with reference to FIGS. 1-7.

FIG. 1 illustrates pest control system 20. System 20 is arranged to protect building 22 from damage due to pests, such as subterranean termites. System 20 includes a number of pest control devices 110 positioned about building 22. In FIG. 1, only a few of devices 110 are specifically designated by reference numerals to preserve clarity. System 20 also includes interrogator 30 to gather information about devices 110. Data gathered from devices 110 with interrogator 30 is collected in Data Collection Unit (DCU) 40 through communication interface 41.

Figure 2:
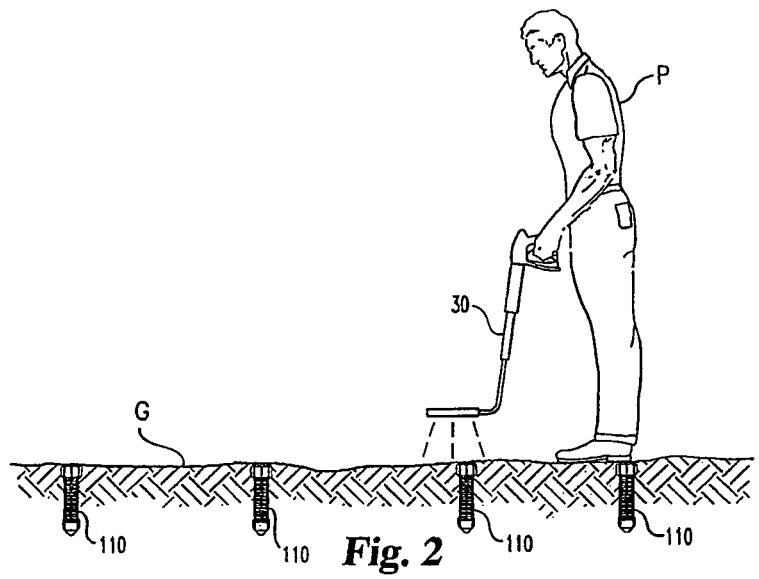
FIG. 2 is a view of selected elements of the system of FIG. 1 in operation.

Referring additionally to FIG. 2, certain aspects of the operation of system 20 are illustrated. In FIG. 2, a pest control service provider P is shown operating interrogator 30 to interrogate pest control devices 110 located at least partially below ground G using a wireless communication technique. In this example, interrogator 30 is shown in a hand-held form convenient for sweeping over ground G to establish wireless communication with installed devices 110. In an alternative example, interrogator 30 may include contacts that are configured to temporarily engage pest control devices 110 to electrically couple therewith in order to interrogate pest control devices 110. Additional aspects of system 20 and its operation are described below, but first further details concerning a representative pest control device 110 are described with reference to FIGS. 3-7.

Figure 3:
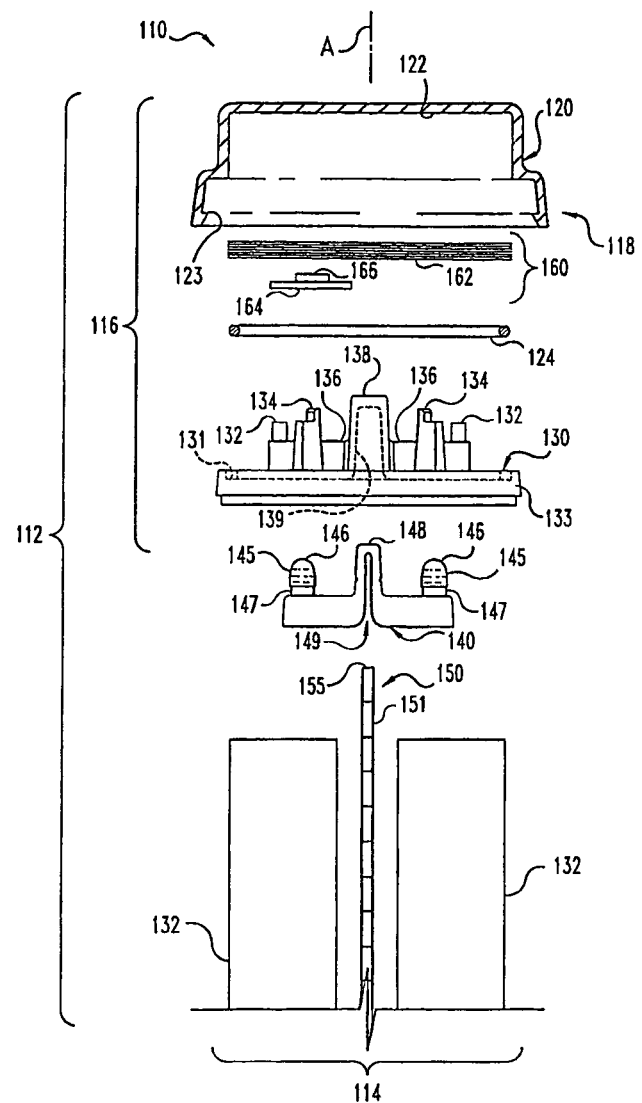
FIG. 3 is an exploded, partial sectional view of a pest monitoring assembly of one embodiment of pest control device.
Figure 4:
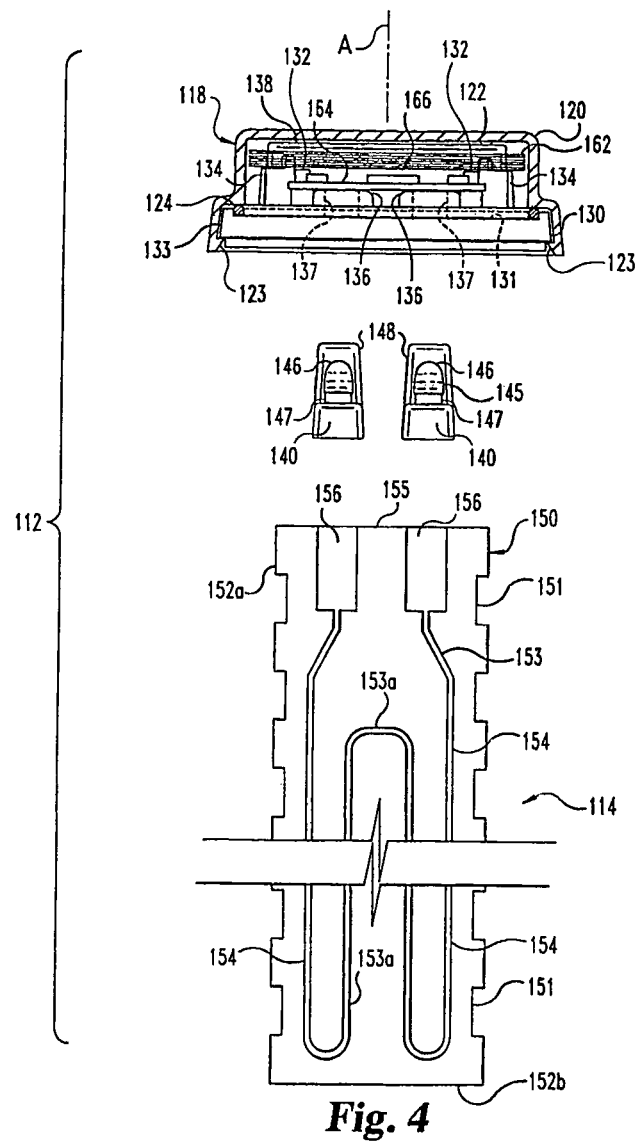
FIG. 4 is an exploded, partial sectional view of the pest monitoring assembly of FIG. 3 along a view plane perpendicular to the view plane of FIG. 3.

FIGS. 3-7 illustrate various features of pest control device 110. To initially detect pests, pest control device 110 is internally configured with pest monitoring assembly 112. Referring more specifically to FIGS. 3 and 4, pest monitoring assembly 112 is illustrated along centerline assembly axis A. Axis A coincides with the view planes of both FIGS. 3 and 4; where the view plane of FIG. 4 is perpendicular to the view plane of FIG. 3.

Pest monitoring assembly 112 includes sensor subassembly 114 below communication circuit subassembly 116 along axis A. Sensor subassembly 114 includes two (2) bait members 132 (see FIGS. 3 and 6). Bait members 132 are each made from a bait material for one or more selected species of pests. For example, bait members 132 can each be made of a material that is a favorite food of such pests. In one example directed to subterranean termites, bait members 132 can each be in the form of a soft wood block without a pesticide component. In other examples for termites, one or more of bait members 132 can include a pesticide, have a composition other than wood, or have a combination of these features. In still other examples where pest control device 110 is directed to a type of pest other than termites, a correspondingly different composition of each bait member 132 is typically used. One or both of bait members 132 can comprise a pesticidal composite material as described hereinabove when it is desired to use a bait member that includes a pesticide.

Figure 6:
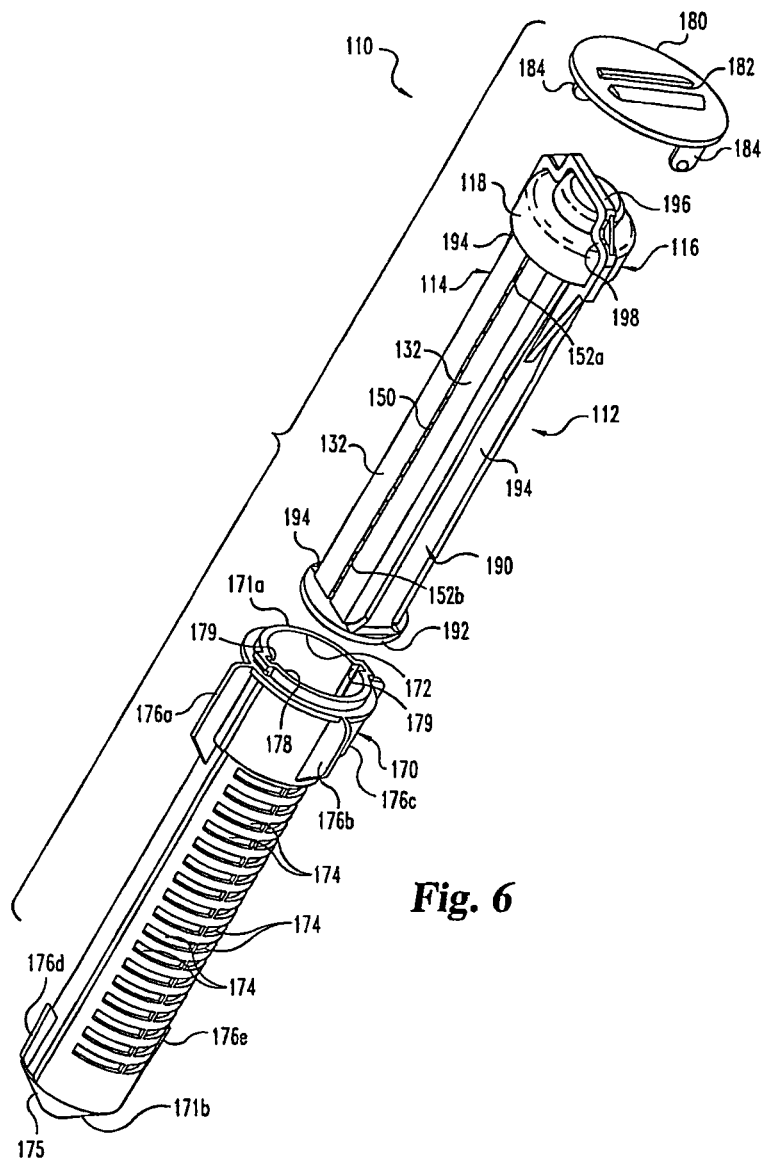
FIG. 6 is an exploded assembly view of the pest control device with the pest monitoring assembly of FIG. 3.

Sensor subassembly 114 also includes sensor 150. Sensor 150 is depicted between bait members 132 in FIGS. 3 and 6; where FIG. 6 is a more fully assembled view of pest control device 110 than FIG. 3. Sensor 150 is generally elongated and has end portion 152a opposite end portion 152b as shown in FIGS. 4 and 6. A middle portion of sensor 150 is represented by a pair of adjacent break lines separating portions 152a and 152b in FIG. 4, and bait members 132 are not shown in FIG. 4 to prevent obscuring the view of sensor 150.

Sensor 150 includes substrate 151. Substrate 151 carries conductor 153 that is arranged to provide sensing element 153a in the form of an electrically conductive loop or pathway 154 shown in the broken view of FIG. 4. Along the middle sensor portion represented by the break lines of FIG. 4, the four segments of pathway 154 continue along a generally straight, parallel route (not shown), and correspondingly join the four pathway segments of end portion 152a ending at one of the break lines with the four pathway segments of end portion 152b ending at another of the break lines. Pathway 154 terminates with a pair of electrical contact pads 156 adjacent substrate edge 155 of end portion 152a.

Substrate 151 and/or conductor 153 are/is comprised of one or more materials susceptible to consumption or displacement by the pests being monitored with pest monitoring assembly 112. These materials can be a food substance, a nonfood substance, or a combination of both for the one or more pest species of interest. Indeed, it has been found that materials composed of nonfood substances will be readily displaced during the consumption of adjacent edible materials, such as bait members 132. In certain embodiments, one or more of substrate 151 or conductor 153 can be composed of a pesticidal composite material as described hereinabove. As substrate 151 or conductor 153 are consumed or displaced, pathway 154 is eventually altered. This alteration can be utilized to indicate the presence of pests by monitoring one or more corresponding electrical properties of pathway 154 as will be more fully described hereinafter. Alternatively, substrate 151 and/or conductor 153 can be oriented with respect to bait members 132 so that a certain degree of consumption or displacement of bait members 132 exerts a mechanical force sufficient to alter the electrical conductivity of pathway 154 in a detectable manner. For this alternative, substrate 151 and/or conductor 153 need not be directly consumed or displaced by the pest of interest.

Pest monitoring assembly 112 further includes circuit subassembly 116 coupled to sensor subassembly 114. Circuit subassembly 116 is arranged to detect and communicate pest activity as indicated by a change in one or more electrical properties of pathway 154 of sensor subassembly 114. Circuit subassembly 116 includes circuit enclosure 118 for housing communication circuitry 160 and a pair of connection members 140 for detachably coupling communication circuitry 160 to sensor 150 of sensor subassembly 114. Enclosure 118 includes cover piece 120, o-ring 124, and base 130, that each have a generally circular outer perimeter about axis A. Enclosure 118 is shown more fully assembled in FIG. 4 relative to FIG. 3. Cover piece 120 defines cavity 122 bounded by inner lip 123. Base 130 defines channel 131 (shown in phantom) sized to receive o-ring 124 and also includes outer flange 133 configured to engage inner lip 123 when base 130 is assembled with cover piece 120 (see FIG. 4).

Figure 5:
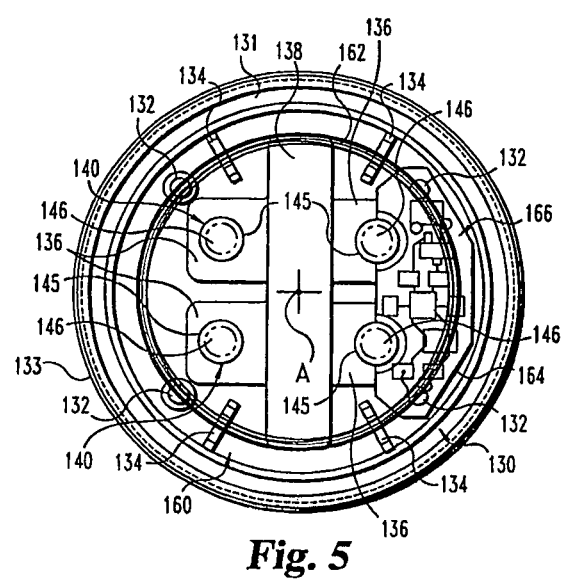
FIG. 5 is a partial, top view of a portion of a communication circuit subassembly of the pest monitoring assembly shown in FIGS. 3 and 4.

Communication circuitry 160 is positioned between cover piece 120 and base 130. Communication circuitry 160 includes coil antenna 162 and printed wiring board 164 carrying circuit components 166. Referring also to FIG. 5, a top view is shown of an assembly of base 130, connection members 140, and wireless communication circuitry 160. In FIG. 5, axis A is perpendicular to the view plane and is represented by like labeled cross-hairs. Base 130 includes posts 132 to engage mounting holes through printed wiring board 164. Base 130 also includes mounts 134 to engage coil antenna 162 and maintain it in fixed relation to base 130 and printed wiring board 164 when assembled together. Base 130 further includes four supports 136 each defining opening 137 therethrough as best illustrated in FIG. 4. Base 130 is shaped with a centrally located projection 138 between adjacent pairs of supports 136. Projection 138 defines recess 139 (shown in phantom in FIG. 3).

Referring generally to FIGS. 3-5, connection members 140 each include a pair of connection nubs 146. Each nub 146 has neck portion 147 and head portion 145 that extend from opposing end portions of the respective connection member 140. For each connection member 140, projection 148 is positioned between the corresponding pair of nubs 146. Projection 148 defines recess 149. Connection members 140 are formed from an electrically conductive, elastomeric material. In one embodiment, each connection member 140 is made from a carbon-containing silicone rubber, such as compound 862 available from TECKNIT, having a business address of 129 Dermody Street, Cranford, N.J. 07016. Nonetheless, in other embodiments, a different composition can be used.

To assemble each connection member 140 to base 130, the corresponding pair of nubs 146 is inserted through a respective pair of openings 137 of supports 136, with projection 148 extending into recess 139. Head portion 145 of each of nubs 146 is sized to be slightly larger than the respective opening 137 through which it is to pass. As a result, during insertion, head portions 145 are elastically deformed until fully passing through the respective opening 137. Once head portion 145 extends through opening 137, it returns to its original shape with neck 147 securely engaging the opening margin. By appropriate sizing and shaping of head portion 145 and neck portion 147 of nubs 146, openings 137 can be sealed to resist the passage of moisture and debris when base 130 and connection members 140 are assembled together. As shown in FIG. 5, printed wiring board 164 contacts one nub 146 of each connection member 140 after assembly.

After connection members 140 are assembled with base 130, enclosure 118 is assembled by inserting base 130 into cavity 122 with o-ring 124 carried in channel 131. During insertion, cover piece 120 and/or base 130 elastically deform so that flange 133 extends into cavity 122 beyond inner lip 123, such that cover piece 120 and base 130 engage each other with a "snap-fit" type of connection. The angled profile of the outer surface of base 130 facilitates this form of assembly. Once cover piece 120 and base 130 are connected in this manner, o-ring 124 provides a resilient seal to resist the intrusion of moisture and debris into cavity 122. The inner surface of cover piece 120 engaged by base 130 has a complimentary profile that can also assist with sealing.

After communication circuit subassembly 116 is assembled, sensor 150 is assembled to subassembly 116 by asserting end portion 152a into recess 149 of each connection member 140 carried by base 130. Connection members 140 are sized to be slightly elastically deformed by the insertion of end portion 152a into recess 149, such that a biasing force is applied by connection members 140 to end portion 152a to securely hold sensor 150 in contact therewith. Once end portion 152a is inserted into connection members 140, each pad 156 is electrically contacted by a different one of connection members 140. In turn, each nub 146 that contacts printed wiring board 164 electrically couples pathway 154 to printed wiring board 164.

Referring to FIG. 6, an exploded view of pest control device 110 and pest monitoring assembly 112 is depicted. In FIG. 6, sensor subassembly 114 and circuit subassembly 116 are shown assembled together and nested in carrying member 190 to maintain pest monitoring assembly 112 as a unit. Carrying member 190 is in the form of a frame that includes base 192 attached to opposing side members 194. Only one of side members 194 is fully visible in FIG. 6, with the other extending from base 192 along the hidden side of pest monitoring assembly 112 in a like manner. Side members 194 are joined together by bridge 196 opposite base 192. Bridge 196 is arranged to define a space 198 contoured to receive the assembled enclosure 118 of circuit subassembly 116.

Pest control device 110 includes housing 170 with removable cap 180 arranged for placement in the ground as shown, for example, in FIG. 2. Housing 170 defines chamber 172 intersecting opening 178. Pest monitoring assembly 112 and carrying member 190 are sized for insertion into chamber 172 through opening 178. Housing 170 has end portion 171a opposite end portion 171b. End portion 171b includes tapered end 175 to assist with placement of pest control device 110 in the ground as illustrated in FIG. 2. End 175 terminates in an aperture (not shown). In communication with chamber 172 are a number of slots 114 defined by housing 170. Slots 174 are particularly well-suited for the ingress and egress of termites from chamber 172. Housing 170 has a number of protruding flanges a few of which are designated by reference numerals 176a, 176b, 176c, 176d, and 176e in FIG. 6 to assist with positioning of pest control device 110 in the ground.

Once inside chamber 172, pest monitoring assembly 112 can be secured in housing 170 with cap 180. Cap 180 includes downward prongs 184 arranged to engage channels 179 of housing 170. After cap 180 is fully seated on housing 170, it can be rotated to engage prongs 184 in a latching position that resists disassembly. This latching mechanism can include a pawl and detent configuration. Slot 182 can be used to engage cap 180 with a tool, such as a flat-bladed screwdriver, to assist in rotating cap 180. It is preferred that carrying member 190, base 130, cover piece 120, housing 170, and cap 180 be made of a material resistant to deterioration by expected environmental exposure and resistant to alteration by the pests likely to be detected with pest control device 110. In one form, these components are made from a polymeric resin like polypropylene or CYCOLAC AR polymeric plastic material available from General Electric Plastics, having a business address of One Plastics Avenue, Pittsfield, Mass. 01201.

Figure 7:
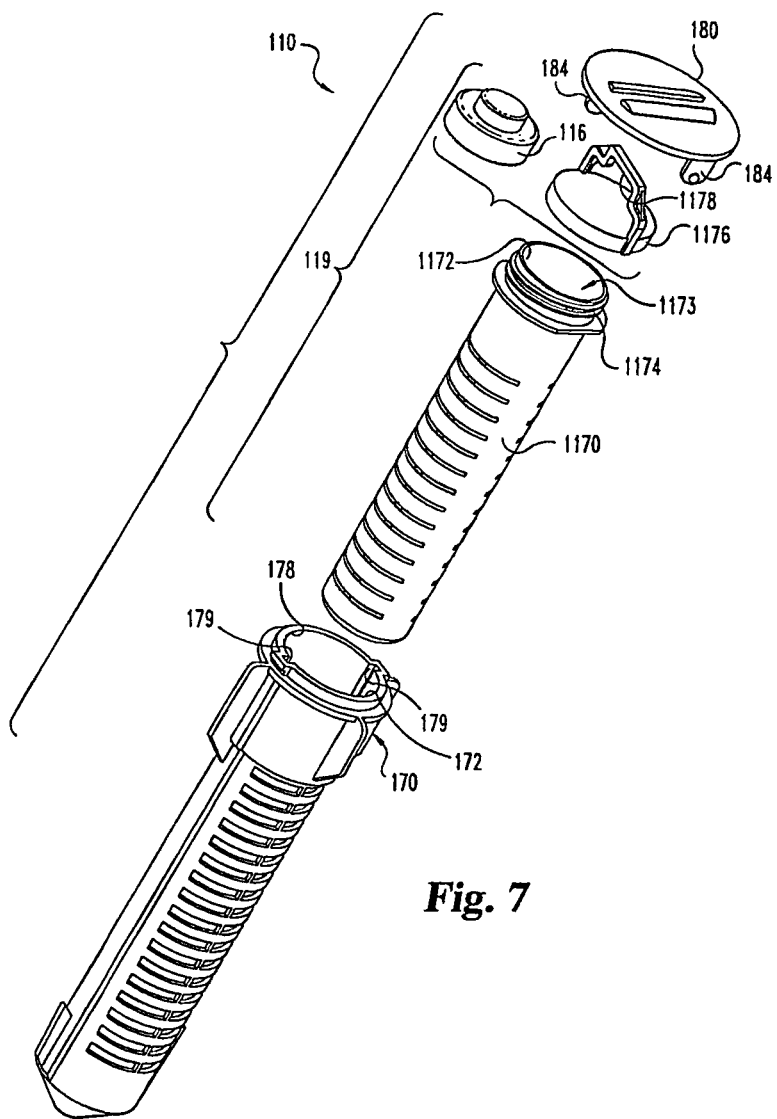
FIG. 7 is an exploded assembly view of the pest control device with a pesticide delivery assembly in place of the pest monitoring assembly of FIG. 3.

Typically, pest monitoring assembly 112 is placed in chamber 172 after housing 170 is at least partially installed in the ground in the region to be monitored. Assembly 112 is configured to detect and report pest activity. In one mode of operation, pest control device 110 is reconfigured to deliver a pesticide after pest activity is detected with pest monitoring assembly 112. FIG. 7 is an exploded assembly view of one example of such a reconfiguration. In FIG. 7, pest control device 110 utilizes pesticide delivery assembly 119 as a substitute for pest monitoring assembly 112 after pest activity has been detected. Substitution begins by rotating cap 180 in a direction opposite that required to latch it, and removing cap 180 from housing 170. Typically, the removal of cap 180 is performed with housing 170 remaining at least partially installed in the ground. Pest monitoring assembly 112 is then extracted from housing 170 by pulling carrying member 190. It has been found that application of pest control device 110 to pests such as termites can lead to the accumulation of a substantial amount of dirt and debris in chamber 172 before pest monitoring assembly 112 is removed. This accumulation can hamper the removal of pest monitoring assembly 112 from chamber 172. As a result, member 190 is preferably arranged to withstand at least 40 pounds (lbs.) of pulling force, and more preferably at least 80 lbs. of pulling force.

After pest monitoring assembly 112 is removed from chamber 172, pesticide delivery assembly 119 is placed in chamber 172 of housing 170 through opening 178. Pesticide delivery assembly 119 includes pesticide bait tube 1170 defining chamber 1172. Chamber 1172 contains pesticide bearing matrix member 1173, which can be composed of the pesticidal composite material described hereinabove. Tube 1170 has a threaded end 1174 arranged for engagement by cap 1176, which has complimentary inner threading (not shown). Cap 1176 defines aperture 1178. Circuit subassembly 116 is detached from sensor 150 before, during, or after removal of pest monitoring assembly 112 from housing 170. Aperture 1178 is accordingly sized and shaped to securely receive circuit subassembly 116 after disassembly from pest monitoring assembly 112. After pesticide delivery assembly 119 is configured with circuit subassembly 116, it is placed in chamber 172, and cap 180 can re-engage housing 170 in the manner previously described.

In view of the above, a person skilled in the art will appreciate that the present application in one aspect provides a pest control device that includes a pesticidal bait operable to be consumed or displaced by one or more species of pest; and a housing at least partially enclosing said bait. The pesticidal bait comprises a composite material including a plastic structural matrix, a cellulosic food material contained within the matrix that is palatable to the pest and a pesticide contained within the matrix that is toxic to the pest. The device can also include a pest sensing circuit or be configured to alternatingly include a pest sensing circuit and a pesticidal bait. In another aspect, the application provides a pest control system that includes at least two pest control devices each arranged to be spaced apart from one another in an area to be protected from one or more pests. At least one of the pest control devices includes, or is configured to alternatingly include, a bait that is operable to be consumed or displaced by the pest and that includes a composite material including a plastic structural matrix, a cellulosic food material contained within the matrix that is palatable to the pest and a pesticide contained within the matrix that is toxic to the pest.

In another aspect, the application provides a method that includes: (1) providing a pest control device including a pesticidal bait for one or more species of pest, the bait including a composite material including a plastic structural matrix, a cellulosic food material contained within the matrix that is palatable to the pest and a pesticide contained within the matrix that is toxic to the pest; and (2) installing the device in an area to be protected from the pests. In one manner of practicing the method, the device is one that further includes a pest sensor and communication circuitry coupled to the pest sensor. In one example, the sensor includes a pest sensing circuit, and the pest sensing circuit includes an electrically conductive loop arranged to be altered during consumption or displacement of the bait for the pest control devices. The loop is coupled to the communication circuitry to provide a two-state signal, a first state of the signal corresponding to an electrically open condition of the loop, and a second state of the signal corresponding to an electrically closed condition of the loop.

In another aspect of the present application, a composite material described herein can be used as a wood substitute material for structural applications that typically call for the use of lumber. The wood substitute material includes a composite material comprising a plastic structural matrix, a cellulosic food material contained within the matrix that is palatable to the pest and a pesticide contained within the matrix that is toxic to the pest. A composite material as described herein can be used as a wood substitute for structural components, such as, for example, structural parts for windows and doors, moldings, or fascia. When the wood substitute material is consumed or displaced by a wood-destroying pest, the pesticide therein will operate to kill some or all of the wood-destroying pests, thereby preventing further damage to the wood substitute material.

The subject matter of the present application will be further described with reference to the following specific Examples. It will be understood that these Examples are intended to be illustrative and not restrictive in nature.

EXAMPLES

Example One

Production of Extruded Composite Materials (Run 1)

Purified cellulose was obtained from International Fiber as several fiber lengths and bulk densities. The fibers tested included AlphaCel BH100, AlphaCel BH200, briquetted BH100, SolkaFloc special granular and SolkaFloc fine granular. For some runs, the AlphaCel BH100 was briquetted to form material of higher bulk density. SolkaFloc fine granular and special granular cellulose were found to be suitable starting materials for mixture with the thermoplastic to form a compounded extruder feed stock.

Table 1 below shows the fibers that were tested in the studies described herein. The studies have all produced products that have been well accepted by termites as measured by mass of the extruded material consumed when compared with MD-499, the aspen wood blocks currently used in SENTRICON® Termite Stations. Different lengths and physical forms of purified cellulose fiber were tested in attempts to identify the best fiber and fiber form for use in the extrusion process.

TABLE 1

Fibers Tested in Extrusion Process

| Cellulose Fiber ED | Length (μm) | Fiber Form | Comments |
|---|---|---|---|
| AlphaCel BH-100 | 40 | Powder | Fiber low bulk density - does not process well, bridges in feeders |
| AlphaCel BH-200 | 35 | Powder | Fiber low bulk density - does not process well, bridges in feeders |
| AlphaCel C-40 | 150 | Flakes | Fiber density higher, processed well, some areas of untreated fiber (chunks of fiber) |
| AlphaCel C-10 | 400 | Flakes | Fiber density higher, processed well, some areas of untreated fiber (chunks of fiber) |
| SolkaFloc Special Granular | 75 | Granules | Fine granules process well, bulk density higher so flows well without bridging in feeders |
| Briquetted-AlphaCel BH-100 | 40 | Briquettes | Fiber very dense. Gelimat broke briquettes to mix with thermoplastic. Incomplete break-up observed in final product. |

Reported physical characteristics for the AlphaCell BH-100 material include an average fiber length of 40 microns, water permeability of 3 darcies cc/g (determined using a 20 gram sample at 5 psi), a wet bulk density of 18 pounds per cubic foot and screen analysis of 0% on 40 Mesh, not less than 90% through 100 Mesh and not less than 70% through 200 Mesh.

Reported physical characteristics for the AlphaCell BH-200 material include an average fiber length of 35 microns, bulk volume 2.1-2.6 cc/g, water retention of 3.0% g/g and screen analysis of 0% on 40 Mesh, 93-100% through 100 Mesh and 75-100% through 200 Mesh.

Reported physical characteristics for the AlphaCell C-40 material include an average fiber length of 120 microns, water permeability of 18 darcies cc/g (determined using a 20 gram sample at 5 psi), a wet bulk density of 9 pounds per cubic foot and screen analysis of less than 1% on 40 Mesh, not more than 95% through 100 Mesh and not more than 50% through 200 Mesh.

Reported physical characteristics for the AlphaCell C-10 material include an average fiber length of 290 microns, water permeability of 28 darcies cc/g (determined using a 20 gram sample at 5 psi), a wet bulk density of 6.5 pounds per cubic foot and screen analysis of less than 15% on 40 Mesh, less than 60% through 100 Mesh and less than 25% through 200 Mesh.

Reported physical characteristics for the SolkaFloc Special Granular material include a bulk volume of 28.0 pounds per cubic foot, water retention of 3.5 g/g and screen analysis of not less than 80% on 40 Mesh and not less than 2% through 200 Mesh.

Briquetted AlphaCel BH-100 was made by adding water to AlphaCel BH-100 and forming the material into briquettes using a Komarek compactor. Active version of this material would have hexaflumuron or noviflumuron sprayed onto the powder prior to briquetting.

Several different types of thermoplastic polymers were used in these trials. Examples include Cellulose Acetate Propionate (CAP), Cellulose Acetate Butyrate (CAB) and Polylactic Acid (PLA). These plastics when mixed with cellulose were eaten by the termites. Initial trials were conducted with CAP, which was processed at a temperature of about 180 to 200° C. This temperature is quite high relative to the melting points of Hexaflumuron and Noviflumuron. Processing the matrix at this high temperature in a Gelimat made the product susceptible to charring or possible ignition if mixed at high shear for too long. The high shear increases temperature quickly and at temperatures above about 220° C., the cellulose would char. PLA was processed at approximately 220° C. At this temperature, the cellulose is quite susceptible to charring so attention was turned to CAB.

The polymer CAB (processing temperature 130-140° C.) was selected to reduce the processing temperature of the extrusions, which has multiple benefits. For example, the fiber/thermoplastic matrix is not as susceptible to charring or burning at the lower temperature when processing through the compounding and extrusion step. In addition, processing at these lower temperatures prevents the degradation of temperature sensitive pesticides.

The form and physical state of the thermoplastic polymers were investigated. Pelletized thermoplastic containing plasticizers was used initially. This material worked satisfactorily after the plasticizer content was optimized to produce the best termite feeding of the extruded matrix. Thermoplastic that is available in a powder form was found to mix better with the cellulose fiber and was found easier to compound. Both the CAP and CAB were used as powdered plastics. Different molecular weights of the plastics were mixed to optimize flow of the thermoplastic in the fiber matrix. The mixture of polymers was selected to produce two effects. The high molecular weight polymer was selected to produce structural strength to the profile and the low molecular weight polymer was selected to provide improved flow for wetting and viscosity reduction of the polymer/cellulose melt. The CAB polymers selected were CAB-531-1 (high molecular weight polymer) mixed with CAB-551-0.01 (low molecular weight polymer).

Cellulose Acetate Butyrate CAB-531-1 is a cellulose ester commercially available from Eastman. CAB-531-1 is soluble in a wide range of solvents, and is a relatively flexible resin, requiring lower plasticizer modification than other, less flexible resins. Reported properties of CAB-531-1 include the following:

| Property | Typical Value, Units |
| --- | --- |
| Butyryl Content | 50 wt % |
| Acetyl Content | 2.8 wt % |
| Hydroxyl Content | 1.7% |
| Viscosity$^a$ | 5.6 poise |
| Color$^b$ | 50 ppm |
| Haze$^b$ | 15 ppm |
| Acidity as Acetic Acid | 0.02 wt % |
| Ash Content | 0.05% |
| Refractive Index | 1.475 |
| Heat Test @ 160° C. for 8 hr | Tan melt |
| Melting Point | 135-150° C. |
| Glass Transition Temperature (Tg) | 115° C. |
| Specific Gravity | 1.17 |
| Wt/Vol (Cast Film) | 1.17 kg/L (9.75 lb/gal) |
| Bulk Density | 480 kg/m3 (30 lb/ft3) |
| Poured | |
| Tapped | 787-984 kv/cm (2-2.5 kv/mil) |
| Dielectric Strength | 576 kg/m3 (36 lb/ft3) |
| Molecular Weight$^c$ $M_n$ | 40000 |
| Tukon Hardness | 15 Knoops |

$^a$Viscosity determined by ASTM Method D 1343. Results converted to poises (ASTM Method D 1343) using the solution density for Formula A as stated in ASTM Method D 817 (20% Cellulose ester, 72% acetone, 8% ethyl alcohol).
$^b$Determination of color and haze made on CAB solutions using Pt—Co standard (color) and a monodisperse latex suspension (haze). Analysis performed with a Gardner Model XL-835 colorimeter.
$^c$Polystyrene equivalent number average molecular weight determined by gel permeation chromatography.

Cellulose Acetate Butyrate CAB-551-0.01 is a cellulose ester commercially available from Eastman with high butyryl content and low ASTM(A) viscosity, which significantly affects it solubility and compatibility. CAB-551-0.01 is soluble in styrene and methyl methacrylate monomers and will tolerate more aliphatic and aromatic hydrocarbon diluent than higher viscosity materials. The solubility of CAB-551-0.01 in alcohol/aromatic hydrocarbon mixtures permits the choice of a wide range of solvents and solvent combinations. CAB-551-0.01 is a dry, white free-flowing powder convenient to handle. Reported properties of CAB-551-0.01 include the following:

| Property | Typical Value, Units |
| --- | --- |
| Butyryl Content | 53 wt % |
| Acetyl Content | 2 wt % |
| Hydroxyl Content | 1.5% |
| Viscosity$^a$ | 0.038 poise |
| Color | 100 ppm |
| Haze | 25 ppm |
| Acidity as Acetic Acid | 0.02 wt % |
| Melting Point | 127-142° C. |
| Glass Transition Temperature (Tg) | 85° C. |
| Char Point | 260° C. |
| Wt/Vol (Cast Film) | 1.16 kg/L (9.67 lb/gal) |
| Molecular Weight$^b$ $M_n$ | 16000 |
| Tukon Hardness | 15 Knoops |

$^a$Viscosity determined by ASTM Method D 1343. Results converted to poises (ASTM Method D 1343) using the solution density for Formula A as stated in ASTM Method D 817 (20% Cellulose ester, 72% acetone, 8% ethyl alcohol).
$^b$Polystyrene equivalent number average molecular weight determined by gel permeation chromatography.

Calcium stearate was used as a lubricant in the extrusions. This material mixes well with the fiber/thermoplastic matrix and assists flow through the extrusion die. The calcium stearate has a melting temperature close to that of the extrusion matrix and lubricates the flow of matrix through the die quite well. Additional lubricants, such as, for example, other metal stearates and other waxes or commercial lubricants are believed to suitable alternatives to calcium stearate for extrusion and will be investigated in subsequent experiments. Lubricants that do not interfere significantly with termite feeding are preferred.

Processing the fiber of the extrusions included applying the pesticide to the fiber using a ribbon blender. A 50% concentrate of either Hexaflumuron or Noviflumuron was sprayed on the fiber to assure even mixing of the pesticide with the fiber. Concentrations were adjusted to account for the concentration of fiber relative to the total matrix composition to deliver approximately 0.5% pesticide in the extruded composite material. An estimated additional amount of pesticide was included to account for loss of pesticide in processing. Processing was also accomplished using air milled technical mixed with calcium stearate and then this mixture added to the compounded fiber/thermoplastic. One other method for incorporation of pesticide is to compound the fiber and thermoplastic, then add the calcium stearate and spray the pesticide on the complete matrix prior to extrusion. All methods produced a finished extruded profile containing the pesticide.

Make up of the extrusion composite material was performed in a batch process. The mixtures were prepared by weighing cellulose and fiber into bins. These bins were dumped in batches of about 80 lbs into the Gelimat for compounding. The compounded matrix was dumped from the Gelimat onto a conveyor, passed through a compression roller while the matrix was still hot to increase the bulk density of the matrix and then this matrix was broken up into feed stock for the extruder. Multiple batches of the same mixture were run through the Gelimat and accumulated until extruded. Extrusion was conducted in a 65 mm Cincinnati Milacron twin screw extruder with a short coupling to a 0.8 inch circular die. After exiting the die, the extruded rod was passed through a cooling chamber and the profile was cooled with sprays of chilled water. After the cooling chamber, the rod was passed into a puller after which the rods were cut to a pre-determined size.

Table 2 below shows the composition and layout for one set of composite materials prepared and tested.

Formulation 1 (Blank Control Pre-extrusion) was made in Run #1 by compounding SolkaFloc prills (in Gelimat) with CAB without any pesticide present. After compounding, Ca stearate was added, and then the mixture was extruded.

Formulation 2 (Hexaflumuron on Fiber) was made in Run #2 by diluting Hexaflumuron 50% concentrate (liquid) with water and spraying the diluted mixture on SolkaFloc prills. Resulting mixture was then compounded, Ca stearate was added, and then the mixture was extruded.

Formulation 3 (Hexaflumuron as solid in Ca Stearate) was made in Run #3 by blending solid, milled hexaflumuron technical (99+ % pure) with Ca stearate and this mixture was blended with a compounded prill/CAB mixture, then extruded.

Formulation 4 (Noviflumuron on fiber) was made in Run #4 using the same process as that used to make Formulation 2, with the exception that noviflumuron 50% concentrate was substituted for hexaflumuron 50% concentrate.

Formulation 5 (Novi on Ca Stearate) was made in Run #5 using the same process as that used to make Formulation 3, wit the exception that milled noviflumuron technical (99+ % pure) was substituted for hexaflumuron technical.

Formulation 6 (Novi sprayed on compounded matrix) was made in Run #6 by compounding SolkaFloc prills (in Gelimat) with CAB. Ca Stearate was mixed with the post-compounded batch, then diluted noviflumuron 50% concentrate was spray applied. Finally the mixture was extruded.

Extruded samples were produced at Teel Plastics. The fiber and plastic were mixed in a Gelimat, a high shear mixer for solids, to compound the fiber and plastic. The fiber and plastic are dumped into the Gelimat together, the cycle started and the high shear mixer mixes the components and melts the plastic to initiate the binding of the thermoplastic with the

TABLE 2

Extrusion Runs at Teel Plastics
Teel Plastic, Barbaroo Wisconsin Runs, Compositions and Conditions
Hexaflumuron ("Hexa") and
Noviflumuron ("Novi")as AIs

| Run # | Run (assay of AI on Fiber) | Extrusion Temp. °C. | % Cellu | % CAB | % CA Stear | Expected Insecticide % | Assay % W/W |
|---|---|---|---|---|---|---|---|
| 1 | SolkaFloc Prill/CAB | 130-135 | 68.6 | 29.4 | 2 | Blank | |
| 2 | 1.6% Hexa SolkaFloc Prill/CAB | 130-135 | 68.6 | 29.4 | 2 | 0.63 or > | 0.78 |
| 3 | 0.63 solid Hexa SolkaFloc Prill/CAB | 130-135 | 68.6 | 29.4 | 2 | 0.55 or > | 0.475 |
| 4 | 1.6% Novi SolkaFloc Prill/CAB | 130-135 | 68.6 | 29.4 | 2 | 0.63 or > | 0.774 |
| 5 | 0.63% solid Novi SolkaFloc Prill/CAB | 130-135 | 68.6 | 29.4 | 2 | 0.55 or > | 0.502 |
| 6 | 1.26% Liq Novi SolkaFloc Prill/CAB | 130-135 | 68.6 | 29.4 | 2 | 0.55 or > | 0.628 |

Batches were prepared by mixing the fiber with the CAB (a 50/50 mix of CAB 531-1 with CAB 551-0.01) and running the batches through the Gelimat to compound the mixture. After mixing and heating in the Gelimat, the batch was dumped onto a conveyor to a paired roller to compress the compounded mixture. The densified mixture was passed to a cutter to produce dry, compounded feed material for the extruder. The combined Gelimat batches were then weighed and placed in a ribbon blender where Calcium Stearate was added. If the pesticide was to be added after compounding, the pesticide was mixed with the Calcium Stearate and the mixture added to the compounded matrix. After mixing, the completed matrix was fed into the twin screw extruder and extruded to produce the final profile. The extruded profile was cooled in a spray tank (about 30 ft. long), passed through a caterpillar puller to keep the profile moving and the profile then cut into the desired lengths.

fiber. The high shear mixing rapidly increases the temperature of the mixture in the Gelimat, driving off water and melting the plastic which binds with the fiber. The compounded matrix was then mixed with Calcium Stearate lubricant and extruded through a Cincinnati Milacron 65 m twin screw extruder. The dies used were varied and greater or less success was obtained depending on the length of the die and the amount of movement and flow the extruding material was subjected to as the matrix passed through the die. We found that in general, the shorter the length of the die and the fewer the impediments to the flow, the better for extruding a profile. Incorporation of the active ingredients was optimized in the extruder at Teel Plastics with a short, straight through die with no impediments such as a spiders or splitters in the die.

As discussed above, and listed in Table 1, several fibers provided by International Fibers have been investigated. In general, the fiber length appears to have little effect on the profiles produced. The larger impact is the fiber density and form. Fiber with low bulk density is difficult to feed and handle. The granulated material flows well and is quite easy to handle with a minimum of dusting.

Bioassays of the samples produced as described in Example 1 were conducted to test the palatability and efficacy of the materials produced. The studies performed, discussed in more detail in Examples 2 and 3, were standard one-way continuous no-choice and limited choice exposure tests. The samples were divided based on active ingredient into two trials. The Noviflumuron samples were run for four weeks since Noviflumuron usually is faster acting and the Hexaflumuron samples were run for six weeks. The extruded Noviflumuron-containing composite materials exhibited toxicity to the termites.

The experiments described in Examples 2 and 3 demonstrate that the manufacturing process for the composite materials produce an extruded monitor or bait well accepted by termites. The extruded composite materials were always much better accepted than wood in all the bioassays conducted. These studies also show it is possible to incorporate active ingredient in an extruded profile and maintain insecticidal activity against termites.

Example Two

Acceptance and Efficacy of Extruded Hexaflumuron Composite Material

One-way continuous no-choice and limited exposure choice tests were performed to determine comparative consumption and efficacy of extruded Hexaflumuron formulations over 42 days with regard to subterranean termite species *Reticulitermes flavipes*. Specifically, these tests measure the feeding response (consumption—mg) and resultant mortality of *Reticulitermes flavipes* subterranean termites in no-choice (Study #1) and 7-day limited choice-feeding (Study #2) tests to extruded composite material formulations containing Hexaflumuron.

Study #1—Continuous Force-Feeding (No-Choice) Exposure

Figure 8:
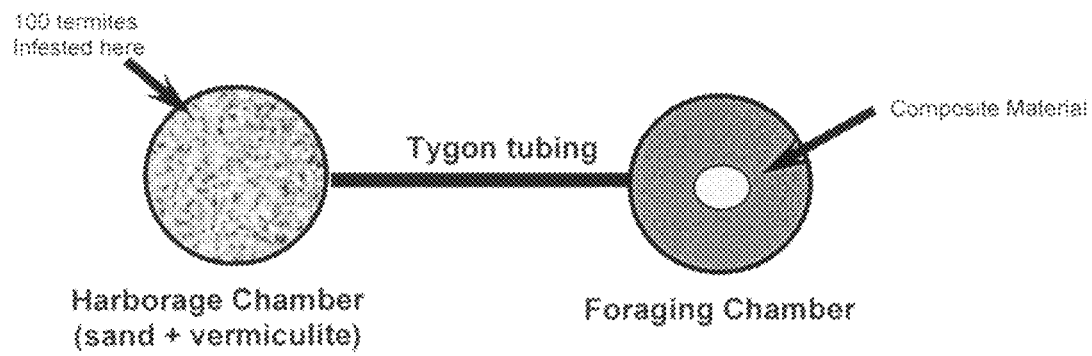
FIG. 8 is a schematic representation of a first test set-up as described in the Examples.

Test Set-up: Standard one-way no-choice test. The set-up for this test is shown in FIG. 8. Study was held in Walk-in Coviron kept at 26° C. and 60% RH. The test included 6 reps, 100 termites/rep, held for 42 days. Three controls of each treatment were held for weight correction.

Species: *R. flavipes*

Treatments—Consumption & Survivorship Graded After 6 Weeks (42 Days)

1. Extruded Formulation 1—Blank.
2. Extruded Formulation 2—Hexaflumuron on Fiber, Assay=0.78%
3. Extruded Formulation 3—Hexaflumuron as solid in Ca Stearate, Assay—0.475%.
4. Blank PTC Briquettes control.
5. Shatter PTC bait containing 0.5% Hexaflumuron. Shatter™ (Dow AgroSciecnes LLC.) bait is a commercially available alpha-cellulose bullet that includes 0.5% hexaflumuron. Shatter bait can also be referred to as "Shatter PTC bait" because the alpha-cellulose material included therein is referred to as preferred textured cellulose.

As used herein, the term "Blank" is used to refer to a test material that does not include any hexaflumuron or any other active agent ("AI"). For example, Extruded Formulation 1 in the above list is an extruded composite material that includes the identified cellulosic food material and the identified plastic matrix, but does not include any AI. Similarly, the term "Blank PTC Briquettes control" refers to briquettes of "preferred textured cellulose" ("PTC") that does not include any AI.

Results and Discussion for Study 1—Continuous No-Choice:

TABLE 3

Continuous Force-Feeding (No-Choice) Exposure
Feeding Response of *R.. flavipes* to Various Bait Matrix
Formulations and Resultant Efficacy after 42 days

| Treatment | mg consumed after 42 days (mean ± SEM)* | No. Survivors/100 after 42 days (mean ± SEM)* | % Corrected Mortality (Compared to Extruded Formulation 1 Control)** |
|---|---|---|---|
| Extruded Formulation 1 (Blank) | 201.27 ± 33 a | 41.33 ± 6.75 a | — |
| Extruded Formulation 2 (Hex on fiber) | 140.11 ± 21.6 cd | 8.0 ± 4.07 b | 80.64 |
| Extruded Formulation 3 (Hex in Ca Stearate) | 159.07 ± 19.3 bc | 12.83 ± 4.92 b | 69.34 |
| Shatter (0.5% Hex) | 127.73 ± 38.1 d | 14.83 ± 6.78 b | 64.19 |
| Blank PTC Briquettes | 169.43 ± 42.8 b | 37 ± 9.14 a | 10.48 |

Each treatment replicated 6 times (100 termites per rep)
*Within these columns, means followed by same letter are not significantly different (ANOVA + LSD; p > 0.10).
SEM = Standard Error of the Mean
**Corrected via Abbott's formula For the continuous no-choice test (results listed in Table 3), *R. flavipes* readily consumed the extruded bait formulations; the blank extruded bait was consumed at a rate that was significantly greater than blank PTC. The formulations containing Hexaflumuron (Formulations 2, 3 and Shatter) were consumed at a lower rate than the blank extruded material (Formulation 1) over the 42-day test, but this lower consumption is most likely due to the toxic effect of the Hexaflumuron in these formulations affecting the consumption rate over the 42-day test. The formulations containing Hexaflumuron had significant mortality vs. the controls but they were not significantly different from each other. Numerically, Extruded Formulation 2 had the greatest corrected mortality after 42 days at 80.64% followed by extruded formulation 3 at 69.34% and Shatter at 64.19%. It was noted that the surviving termites exposed to the extruded formulations containing Hexaflumuron had symptoms of chitin synthesis inhibitor effects in that may appears slow/sick and were pale in color. The surviving termites exposed to the blank extruded material appeared normal in appearance. Consistent with a prior study, the blank extruded formulation control (Formulation 1) was consumed significantly more than the blank PTC briquettes control and numerically there were more survivors for the blank extruded material.

Study #2—Limited Choice Exposure

Figure 9:
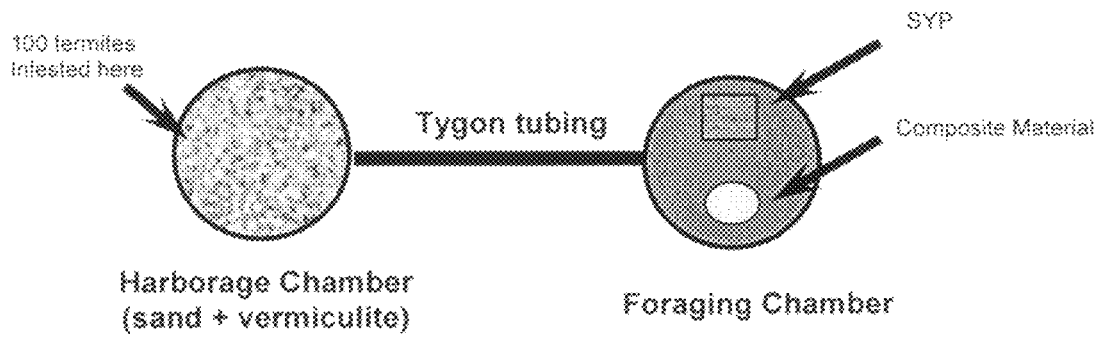
FIG. 9 is a schematic representation of a second test set-up as described in the Examples.

Test Set-up: Standard one-way paired-choice efficacy test vs. untreated southern yellow pine (SYP—½" size). The set-up for this test is shown in FIG. 9. Study was held in Walk-in Coviron kept at 26° C. and 60% RH. The test included 6 reps, 100 termites/rep, held for 42 days. After 7 days, the composite material and the SYP were removed and replaced with blank filter paper for the remaining duration of the test. Three controls of each treatment were held for weight correction.

Species: *R. flavipes*

Treatments—Consumption & Survivorship Graded After 6 Weeks (42 Days)
1. Extruded Formulation 1—Blank.
2. Extruded Formulation 2—Hexaflumuron on Fiber, Assay=0.78%
3. Extruded Formulation 3—Hexaflumuron as solid in Ca Stearate, Assay—0.475%.
4. Blank PTC Briquettes control.
5. Shatter PTC bait containing 0.5% Hexaflumuron.

Results and Discussion for Study 2: Limited Choice Exposure:

Results from these two tests show that the extruded Hexaflumuron formulations are readily accepted and consumed at a very high rate, and extruded formulations containing Hexaflumuron were preferred over SYP. In addition, the extruded formulations containing Hexaflumuron had significantly more activity than controls and had numerically higher but statistically similar effect compared to Shatter. Termite mortality was numerically higher but statistically similar for the extruded+Hexaflumuron formulations vs. Shatter bait.

Example Three

Acceptance and Efficacy of Extruded Noviflumuron Composite Material

One-way continuous no-choice (Study #1) and limited choice exposure (Study #2) tests were performed to determine comparative consumption and efficacy of new extruded Noviflumuron formulations over 28 days to *R. falvipes*. These tests were designed for the purpose of determining what is the feeding response (consumption—mg) and resultant mortality of *Reticulitermes flavipes* subterranean termites in no-choice and 7-day limited choice-feeding tests to a new extruded formulation containing Noviflumuron, thereby quantifying palatability and efficacy measurements of new extruded composite materials containing Noviflumuron.

Study #1—Continuous Force-Feeding (No-Choice) Exposure

Test Set-up: Standard one-way no-choice test. Test set-up is shown in FIG. 8. Study was held in Walk-in Coviron kept at

TABLE 4

Choice Feeding/Efficacy Test.
Comparative Feeding Response of *R.. flavipes* to Various Bait Matrix Formulations and Untreated SYP after 7 days, and Resultant Efficacy after 42 days

| Paired Choice* | mg consumed after 7 days (mean ± SEM)* | Palatability Ratio, mg Treatment ± mg Untreated SYP | No. Survivors/100 after 42 days (mean ± SEM)** | % Corrected Mortality (Compared to Formulation 1 Extruded Control)^ |
|---|---|---|---|---|
| Formulation 1 (Blank) vs. Untreated SYP | 25.97 ± 6.76 a<br>7.97 ± 2.87 b<br>(p value = 0.044) | 3.26 | 20.83 ± 6.76 a | — |
| Formulation 2 (Hex on fiber) vs. Untreated SYP* | 26.17 ± 5.2 a<br>7.38 ± 32.1 b<br>(p value = 0.054) | 3.55 | 4.83 ± 4.83 c | 76.8 |
| Formulation 3 (Hex in Ca Stearate) vs. Untreated SYP | 22.03 ± 8.33 a<br>3.69 ± 1.52 b<br>(p value = 0.063) | 5.97 | 8.67 ± 4.11 bc | 58.38 |
| Shatter (0.5% Hex) vs. Untreated SYP | 31.97 ± 4.41 a<br>5.38 ± 2.29 b<br>(p value = 0.008) | 5.94 | 11.67 ± 5.10 abc | 43.9 |
| Blank PTC Briquettes vs. Untreated SYP | 25.90 ± 5.43 a<br>3.29 ± 1.73 b<br>(p value = 0.015) | 7.87 | 18.5 ± 8.79 ab | 11.19 |

Each choice test replicated 6 times (100 termites per rep).
*4 reps for consumption
*Within each choice test, means followed by same letter are not significantly different (T-Test; p > 0.10) SEM = Standard Error of the Mean
**Within this column, means followed by same letter are not significantly different (ANOVA + LSD; p > 0.10).
^Corrected via Abbott's formula The limited choice test results (Table 4) show that all treatments were consumed significantly more than SYP. The controls did not perform well in this limited choice test. The survivorship results for this limited choice test were similar to what was found in the continuous no-choice test (Table 3); the extruded formulations containing Hexaflumuron were significantly better than the blank extruded and numerically better than Shatter.

held for 28 days. Three controls of each treatment were held for weight correction.

Species: *R. flavipes*

Treatments—Consumption & Survivorship was Graded After 4 Weeks (28 Days)
1. Extruded Formulation 1—Blank control
2. Extruded Formulation 4—Noviflumuron on Fiber, Assay=0.774% .

3. Extruded Formulation 5—Noviflumuron on Ca Stearate, Assay=0.502%.
4. Extruded Formulation 6—Noviflumuron sprayed on compounded matrix, Assay=0.628%
5. Recruit IV PTC bait containing 0.5% Noviflumuron
6. Blank PTC Briquettes.

Results and Discussion for Study 1—Continuous No-Choice:

TABLE 5

Continuous Force-Feeding (No-Choice) Exposure.
Feeding Response of *R.. flavipes* to Various Bait Matrix
Formulations and Resultant Efficacy after 28 days

| Treatment | mg consumed after 28 days (mean ± SEM)* | No. Survivors/100 after 28 days (mean ± SEM)* | % Corrected Mortality (Compared to Extruded Formulation 1 Control)** |
|---|---|---|---|
| Extruded Formulation 1 (Blank) | 161.39 ± 6.40 a | 87 ± 1.67 a | — |
| Extruded Formulation 4 (Novi on fiber) | 127.95 ± 6.71 b | 53.16 ± 2.70 b | 38.9 |
| Extruded Formulation 5 (Novi in Ca Stearate) | 134.84 ± 7.59 b | 51.16 ± 3.77 b | 41.2 |
| Extruded Formulation 6 (Novi sprayed on compounded matrix) | 121.52 ± 7.36 b | 52.83 ± 3.03 b | 39.28 |
| Recruit IV PTC (0.5% Novi) | 47.82 ± 10.3 c | 25.5 ± 8.33 c | 70.69 |
| Blank PTC Briquettes | 118.16 ± 2.96 b | 77.83 ± 3.03 a | 10.54 |

Each treatment replicated 6 times (100 termites per rep).
*Within these columns, means followed by same letter are not significantly different (ANOVA + LSD; p > 0.10). SEM = Standard Error of the Mean
**Corrected via Abbott's formula For the continuous no-choice test (results set forth in Table 5), *R. flavipes* readily consumed the extruded bait formulations containing Noviflumuron at a rate that was statistically equal to that of blank PTC briquettes. Recruit IV was consumed significantly less than the extruded formulations, but this lower consumption is most likely due to the early onset of the toxic effect of the Noviflumuron in the Recruit IV bait. Recruit IV had significantly the greatest mortality after 28 days with an average of 25.5 survivors/100 with the corrected mortality=70.60%. It was noted that the surviving termites exposed to Recruit IV were very sick and near death. The extruded formulations containing Noviflumuron (Formulations 4, 5 & 6) all had similar activity that was significantly better than the controls; with the corrected mortality of the three formulations very consistent in the 39-41% range. At 28 days, it was noted that some of the surviving termites exposed to the extruded Noviflumuron formulations were slowed and showing toxic effects while some appeared normal. These observations were similar across the three formulations. It was interesting to note that the blank extruded formulation (Formulation 1) was consumed significantly more than even the blank PTC briquettes and numerically there were more survivors for the blank extruded material which suggests that the extruded formulation is adequately nutritious for the termites.

Study #2—Limited Choice Exposure

Test Set-up: Standard one-way paired-choice efficacy test vs. untreated southern yellow pine (SYP=½" size). Test set-up is as shown in FIG. 9. Study was held in Walk-in Conviron kept at 26° C. and 60% RH. The test included 6 reps, 100 termites/rep, held for 28 days. After 7 days, bait matrix treatment and SYP were removed and replaced with blank filter paper for the remaining duration of the test. Three controls of each treatment were held for weight correction.

Species: *R. flavipes*

1. Extruded Formulation 1—Blank vs. SYP
2. Extruded Formulation 4—Noviflumuron on Fiber, Assay=0.774% vs. SYP
3. Extruded Formulation 5—Noviflumuron on Ca Stearate, Assay=0.502% vs. SYP
4. Extruded Formulation 6—Noviflumuron sprayed on compounded matrix, Assay=0.628% vs. SYP
5. Recruit IV PTC bait containing 0.5% Noviflumuron vs. SYP
6. Blank PTC Briquettes control vs. SYP Results and Discussion for Study 2: Limited Choice Exposure:

TABLE 6

Choice Feeding/Efficacy Test.
Comparative Feeding Response of *R.. flavipes* to Various Bait Matrix
Formulations and Untreated SYP after 7 days, and Resultant Efficacy after 28 days

| Paired Choice* | mg consumed after 7 days (mean ± SEM)* | Palatability Ratio, mg Treatment + mg Untreated SYP | No. Survivors/100 after 28 days (mean ± SEM)** | % Corrected Mortality (Compared to Formulation 1 Extruded Control) |
|---|---|---|---|---|
| Formulation 1 (Blank) vs. Untreated SYP | 52.02 ± 2.39 a<br>0.00 ± 0.00 b<br>(p value <0.0001) | ∞ | 63 ± 5.46 a | — |
| Formulation 4 (Novi on fiber) vs. Untreated SYP | 39.0 ± 5.2 a<br>40.4 ± 32.1 a<br>(p value = 0.965) | 0.965 | 29.66 ± 4.25 b | 52.93 |
| Formulation 5 (Novi on CA Stearate) vs. Untreated SYP | 44.9 ± 2.60 a<br>18.2 ± 11.7 b<br>(p value = 0.090) | 2.47 | 31.5 ± 2.62 b | 50 |

TABLE 6-continued

Choice Feeding/Efficacy Test.
Comparative Feeding Response of *R.. flavipes* to Various Bait Matrix
Formulations and Untreated SYP after 7 days, and Resultant Efficacy after 28 days

| Paired Choice* | mg consumed after 7 days (mean ± SEM)* | Palatability Ratio, mg Treatment + mg Untreated SYP | No. Survivors/100 after 28 days (mean ± SEM)** | % Corrected Mortality (Compared to Formulation 1 Extruded Control)^ |
|---|---|---|---|---|
| Formulation 6 (Novi sprayed on) vs. Untreated SYP | 48.66 ± 6.24 a<br>0.24 ± 0.24 b<br>(p value = 0.001) | 199 | 30.83 ± 2.69 b | 51.06 |
| Recruit IV PTC (0.5% Novi) vs. Untreated SYP | 50.08 ± 5.03 a<br>8.01 ± 8.01 b<br>(p value = 0.016) | 6.25 | 1.67 ± 1.67 c | 97.35 |
| Blank PTC Briquettes vs. Untreated SYP | 63.63 ± 6.95 a<br>0.00 ± 0.00 b<br>(p value <0.0001) | ∞ | 57.8 ± 8.68 a | 8.25 |

*Each choice test replicated 6 times (100 termites per rep)
*Within each choice test, means followed bysame letter are not significantly different (T-Test; p > 0.10). SEM = Standard Error of the Mean
**Within this column, means followed by same letter are not significantly different (ANOVA + LSD; p > 0.10).
^Corrected via Abbott's formula The limited choice rest results (Table 6) show that all treatments were consumed significantly more than SYP except for Formulation 4. It is believed that the high SYP consumption (40.4 mg) and the high Standard Error of the Mean (SEM) of 32.1 in this choice comparison is an error caused when drying the samples in the oven. A few of the SYP samples visibly lost an excessive amount of sap during the oven drying, which likely resulted in the higher SEM. In addition, when examining the SYP samples there appeared to be little to no visible consumption. Survivorship results for the treatments were similar to what we saw with the continuous no-choice test (Recruit IV>extruded Noviflumuron formulations>controls); however overall more termites died in this study across all of the treatments including the controls. Two different *R. flavipes* colonies were used in the limited choice test than what were used in the continuous no-choice test and colony differences are most likely the reason for the lower overall survivorship in this limited choice test. The condition of the survivors were visibly similar to what we saw with the continuous no-choice test; the Recruit IV survivors were near death while some of the extruded Noviflumuron survivors were visibly slow and affected while some appear normal. Again, these visible effects were noted similarly across the three extruded treatments.

Results from these two tests show that the extruded Noviflumuron formulations are readily accepted and consumed at a very high rate similar to blank PTC. The extruded composite materials gave significant activity vs. the control but were less active than Recruit IV containing 0.5% Noviflumuron at 28 days. The three extruded Noviflumuron formulations were statistically similar for efficacy across the two tests and all had significant activity vs. the controls. The lower activity at 28 days is most likely due to bioavailability of the Noviflumuron in the extruded formulations. Improved formulations that are more bioavailable will be expected to achieve activity similar to Recruit IV.

Example Four

Production of Extruded Composite Materials (Run 2)

A second set of composite material batches were prepared using the same starting materials as described in Example 1. Table 7 below shows the composition and layout for the second set of composite materials prepared.

TABLE 7

| Run # | Run (assay of AI on Fiber) | Extru Temp. °C. | Cellu % | Wt. Cellu | % CAB | Wt. CAB |
|---|---|---|---|---|---|---|
| 7 | SolkaFloc Prill/CAB Blank Run Modified L Die | 130-135 | 68.6 | 480.20 | 29.4 | 205.8 |
| 8 | 0.85% Novi SolkaFloc Prill/CAB Noviflumuron sprayed on Cellulose Modified L Die | 130-135 | 68.6 | 1577.80 | 29.4 | 676.2 |
| 9 | 0.85% Hex SolkaFloc Prill/CAB Hexaflumuron sprayed on Cellulose Modified L Die | 130-135 | 68.6 | 192.08 | 29.4 | 82.32 |

| Run # | Ca Stear | Wt Lub | Prod'n Rate ft/min | Expected % | Assay | Batch Size lbs. | Max Ft. | Num of Parts |
|---|---|---|---|---|---|---|---|---|
| 7 | 2 | 14 | 10 to 15 | Blank | 0 Tested | 700 | 1951.4 | 1672.63 |
| 8 | 2 | 46 | 10 to 15 | 0.5 | 0.79% at Early Part of Run Tested | 2300 | 6411.75 | 5495.79 |
| 9 | 2 | 5.6 | 10 to 15 | 0.5 | 0.58% Tested | 280 | 780.561 | 669.053 |

The extruded composite materials produced in Runs 7-9 are referred to herein as Formulations 7-9, respectively. Bioassays of these Formulations 7-9 were conducted, as discussed in greater detail in Examples 5-9, below.

Example Five

Acceptance and Efficacy of Extruded Hexaflumuron Composite Materials to Two Subterranean Termite Species Efficacy of extruded Hexaflumuron treatment formulations as described in Example 4 (Spray on Cellulose Formulation) to *R. flavipes* & *C. formosanus* were tested.

Test Set-up: Standard One-way no-choice efficacy test with cups, 4 or 6 reps of 100 termites/rep held for 28, 42 or 56 days. All studies were held in Walk-in Conviron at 26° C. and 60% RH. Three controls of each treatment were held for weight correction.

Species: *R. flavipes* and *C. formosanus* (2 colonies of each species used in each test)

Treatments—Consumption & Survivorship was Graded at 6 Weeks (42 Days):

1. Extruded Formulation 7—Blank
2. Extruded Formulation 9—Hexaflumuron Sprayed on Cellulose, Assay=0.58%
3. Shatter PTC bait containing 0.5% Hexaflumuron Each test was replicated 6 times with 100 termites per replicate. Thus, three no-choice tests×six reps=18 one-way units and 1800 termites (*R. flavipes* & *C. formosanus*) were installed for each species. Therefore, for 2 species, 36 one-way units and 3600 termites were required Results:

Results are set forth in Tables 8 (*R. flavipes*) & 9 (*C. formosanus*).

TABLE 8

Continuous Force-Feeding (No-Choice) Exposure. Feeding Response of *R. flavipes* to Various Bait Matrix Formulations Containing Hexaflumuron and Resultant Efficacy after 42 days.

| Treatment | mg consumed after 42 days (mean ± SEM)* | No. Survivors/100 after 42 days (mean ± SEM)^ | % Corrected Mortality (Compared to Extruded Formulation 7 Blank Control)** |
|---|---|---|---|
| Extruded Formulation 7 - Blank | 343.3 ± 22.8 a | 86.67 ± 2.92 a | — |
| Extruded Formulation 9 Hexaflumuron - Sprayed on cellulose, Assay = 0.58% | 207.0 ± 11.9 b | 9.67 ± 2.50 b | 88.84 |
| Shatter PTC bait containing 0.5% Hexaflumuron | 126.0 ± 10.0 c | 3.33 ± 2.06 c | 96.16 |

Each treatment replicated 6 times (100 termites per rep).
*For Consumption, means followed by same letter are not significantly different, (ANOVA + LSD; p > 0.10).
^For Survivors, means followed by the same letter are not significantly different, (Binary Logistic Regression)
**Corrected via Abbott's formula

TABLE 9

Continuous Force-Feeding (No-Choice) Exposure. Feeding Response of *C. formosanus* to Various Bait Matrix Formulations Containing Hexaflumuron and Resultant Efficacy after 42 days.

| Treatment | mg consumed after 42 days (mean ± SEM)* | No. Survivors/100 after 42 days (mean ± SEM)^ | % Corrected Mortality (Compared to Extruded Formulation 7 Blank Control)** |
|---|---|---|---|
| Extruded Formulation 7 - Blank | 90.12 ± 19.0 a | 65.67 ± 2.91 a | — |
| Extruded Formulation 9 Hexaflumuron - Sprayed on cellulose, Assay = 0.58% | 99.68 ± 13.9 a | 59.67 ± 2.33 a | 9.14 |
| Shatter PTC bait containing 0.5% Hexaflumuron | 52.35 ± 0.58 b | 44.67 ± 2.33 b | 31.97 |

Each treatment replicated 3 times (100 termites per rep). 3 additional reps were omitted due to a bad (sick) colony.
*For Consumption, means followed by same letter are not significantly different, (ANOVA + LSD; p > 0.10).
^For Survivors, means followed by the same letter are not significantly different, (Binary Logistic Regression)
**Corrected via Abbott's formula Similar to what was seen previously, R. flavipes actively fed on the extruded formulations with consumption of the extruded formulation containing hexaflumuron (Formulation 9) significantly greater than Shatter. Although mortality was significantly less for the extruded sprayed on cellulose formulation (Formulation 9) in comparison to Shatter, overall corrected control for Formulation 9 was high at 88.84% which was just slightly lower in comparison to Shatter at 96.16% at time of study conclusion (42 days). Control to R. flavipes was greater in this test compared to what was seen previously and this may be due to the higher percentage of hexaflumuron (0.58%) or possibly termite colony differences. Shatter also had greater efficacy in this study which could be a related to variation of different termite colonies or possibly the time of year these tests were run (this study was run mid-late spring/early summer vs. late winter/early spring for earlier study). Trends for C. formosanus (Table 9) were similar to what we saw previously with findings for extruded noviflumuron formulations. Feeding on the extruded formulation with hexaflumuron was greater than Shatter; however Shatter efficacy was significantly higher. Overall efficacy was low for this study and it may have been better to let the study go longer, but a decision was made to break down at 42 days due to the fact that the control was starting to drop off which does happen on occasion during these longer term lab studies.

Example Six

Acceptance and Efficacy of Extruded Noviflumuron Composite Materials to Two Subterranean Termite Species Efficacy of extruded Noviflumuron treatment formulations (Higher Assay Spray on Cellulose Formulation) to R. flavipes & C. formosanus were tested.

Test Set-up: Standard One-way no-choice efficacy test with cups, 4 or 6 reps of 100 termites/rep held for 28, 42 or 56 days. All studies were held in Walk-in Conviron at 26° C. and 60% RH. Three controls of each treatment were held for weight correction. Study #1 was a 6-week test and Study #2 was an 8-week test.

Species: R. flavipes and C. formosanus (2 colonies of each species used in each test)

Treatments (All Tests)—Consumption & Survivorship was Graded After 6 Weeks (42 Days) for Study #1 and 8 Weeks (56 Days) for Study #2:

1. Extruded Formulation 7—Blank
2. Extruded Formulation 8 sprayed on cellulose—Noviflumuron 0.79%
3. Recruit IV PTC containing 0.5% Noviflumuron Each test was replicated 6 times with 100 termites per replicate. For all tests combined, 6 (3 treatments×2 tests/treatment) no-choice set ups×6 reps=36 one-way units with cups and 3600 termites of each species were set-up. Therefore for 2 species, 72 one-way units with cups and 7200 termites total were required.

Results:

Results for R. flavipes (Table 10) show that the higher assay spray on formulation (0.79% noviflumuron) had greater consumption than Recruit IV for both the 42 day and 56 day studies and also efficacy was similar at 42 days (65.77% vs 69.48%, NSD, Binary Logistic Regression) and just slightly lower; 87.58% vs. 100% corrected control for Recruit IV at 56 days, however this difference was significant (Binary Logistic Regression).

TABLE 10

Continuous Force-Feeding (No-Choice) Exposure. Feeding Response of R. flavipes to Various Bait Matrix Formulation Containing Noviflumuron and Resultant Efficacy after 42 & 56 days.

| Treatment (42 day Test) | mg consumed after 42 days (mean ± SEM)* | No. Survivors/100 after 42 days (mean ± SEM)^ | % Corrected Mortality (Compared to Extruded Formulation 7 Blank Control)** |
|---|---|---|---|
| Extruded Formulation 7 - Blank | 265.04 ± 14.6 a | 80.83 ± 4.48 a | — |
| Extruded Formulation 8 - Noviflumuron - Sprayed on cellulose, Assay = 0.79% | 141.93 ± 10.6 b | 27.67 ± 4.35 b | 65.77 |
| Recruit IV bait containing 0.5% Noviflumuron | 105.72 ± 7.94 c | 24.67 ± 7.15 b | 69.48 |

| Treatment (56 day Test) | mg consumed after 56 days (mean ± SEM)* | No. Survivors/100 after 56 days (mean ± SEM)^ | % Corrected Mortality (Compared to Extruded Formulation 7 Blank Control)** |
|---|---|---|---|
| Extruded Formulation 7 - Blank | 324.8 ± 22.2 a | 83.17 ± 5.02 a | — |
| Extruded Formulation 8 - Noviflumuron - Sprayed on cellulose, Assay = 0.79% | 161.5 ± 13.2 b | 10.33 ± 2.33 b | 87.58 |
| Recruit IV bait containing 0.5% Noviflumuron | 79.84 ± 10.7 c | 0.00 ± 0.00 c | 100 |

Each treatment replicated 6 times (100 termites per rep).
*For Consumption, means followed by same letter are not significantly different, (ANOVA + LSD; p > 0.10).
^For Survivors, means followed by the same letter are not significantly different, (Binary Logistic Regression)
**Corrected via Abbott's formula Also similar to what was found in the studies completed previously, the consumption by *C. formosanus* was significantly more for the extruded formulations in comparison to Recruit IV, but the corrected mortality compared to control was significantly lower for Extruded Formulation 8 (assay=0.79% noviflumuron sprayed on cellulose) with results at 0% for Formulation 8 vs. 48.21% for Recruit IV at 42 days and 31.99% for Formulation 8 vs. 85.14% for Recruit IV (Table 11). These lab results again are indicative of what has been recently reported from experimental field trials with extruded materials to *C. formosanus*.

TABLE 11

Continuous Force-Feeding (No-Choice) Exposure. Feeding Response of *C. formosanus* to Various Bait Matrix Formulations Containing Noviflumuron and Resultant Efficacy after 42 & 56 days.

| Treatment (42 day Test) | mg consumed after 42 days (mean ± SEM)* | No. Survivors/100 after 42 days (mean ± SEM)* | % Corrected Mortality (Compared to Extruded Formulation 7 Blank Control)** |
|---|---|---|---|
| Extruded Formulation 7 - Blank | 75.18 ± 17.1 a | 74.67 ± 6.06 a | — |
| Extruded Formulation 8 - Noviflumuron - Sprayed on cellulose, Assay = 0.79% | 52.55 ± 10.7 a | 78.33 ± 2.96 a | 0.0 |
| Recruit IV bait containing 0.5% Noviflumuron | 14.53 ± 2.98 b | 38.67 ± 15.6 b | 48.21 |

| Treatment (56 day Test) | mg consumed after 56 days (mean ± SEM)* | No. Survivors/100 after 56 days (mean ± SEM)* | % Corrected Mortality (Compared to Extruded Formulation 7 Blank Control)** |
|---|---|---|---|
| Extruded Formulation 7 - Blank | 103.01 ± 25.1 a | 74.0 ± 4.16 a | — |
| Extruded Formulation 8 - Noviflumuron - Sprayed on cellulose, Assay = 0.79% | 36.64 ± 20.7 b | 50.33 ± 6.33 b | 31.99 |
| Recruit IV bait containing 0.5% Noviflumuron | 25.19 ± 3.8 b | 11.00 ± 5.86 c | 85.14 |

Each treatment replicated 3 times (100 termites per rep). 3 additional reps were omitted due to a bad (sick) colony.
*For Consumption, means followed by same letter are not significantly different, (ANOVA + LSD; p > 0.10).
^For Survivors, means followed by the same letter are not significantly different, (Binary Logistic Regression)
**Corrected via Abbott's formula Overall for both *R. flavipes* and *C. formosanus*, the extruded formulations containing either hexaflumuron or noviflumuron were generally consumed significantly more than Shatter and Recruit IV. This was true for both the sprayed on cellulose and the incorporated in the cellulose extruded formulations. Differences in consumption between the two extruded formulations were not much different for either species; however *R. flavipes* numerically consumed more extruded material vs. *C. formosanus* when comparing the different tests. Depending on the test, average consumption of one of the extruded formulations may have been more at one evaluation and then in the same test when graded for a different time period (i.e., 42 days vs 56 days) the other extruded formulation may have been consumed more—there was no clear preference between the formulations (sprayed on cellulose vs. incorporated in cellulose for either species.

Mortality was most often significantly less (Binary Logistic Regression analysis) for the extruded formulations of hexaflumuron vs. Shatter and noviflumuron vs. Recruit IV. This was especially true for *C. formosanus* where control was much less (highly significant) than Shatter or Recruit IV. For *R. flavipes*, the differences were not as great and in a few tests, the efficacy was not significantly different vs. Shatter or Recruit IV.

Example Seven

Acceptance and Efficacy of Extruded Noviflumuron and Hexaflumuron Composite Materials to Multiple Subterranean Termite Species Palatability and efficacy of extruded AI-containing composite materials to multiple different termite species was tested to determine whether the key subterranean termite species *Reticulitermes virginicus, C. formosanus, Reticulitermes Hesperus, Reticulitermes speratus* and *Heterotermes aureus* consume (mg) less (p=0.1) of the extruded formulations containing the AIs noviflumuron or hexaflumuron compared to commercial AI-containing baits in no-choice laboratory tests, and to determine whether extruded formulations containing the AIs noviflumuron or hexaflumuron cause significantly less mortality vs. the commercial baits (p=0.05, Binary Logistic Regression) to key subterranean termite species *Reticulitermes virginicus, C. formosanus, Reticulitermes Hesperus, Reticulitermes speratus* and *Heterotermes aureus* in no-choice laboratory tests. The tests comparing extruded composite materials containing noviflumuron to Recruit IV examined data at 4, 6 and 8 weeks. The tests comparing extruded composite materials containing hexaflumuron to Shatter bait examined data at 6 weeks.

Study #1: Consumption & Efficacy of Extruded Noviflumuron Formulations to Additional Termite Species
Species: *R. virginicus, C. formosanus, R. hesperus, H. aureus*
Test Set-up: One-way, continuous no-choice tests, 4-8 reps, 100 termites per rep, 4 and/or, 6 and/or, 8-week data (*R. virginicus* & *C. formosanus*=4, 6, & 8 week data; *R. hesperus* & *H. aureus*=6 week data only)
Treatments
1. Extruded Formulation 1—Blank
2. Extruded Formulation 4—Novi on fiber*, 0.774%
3. Extruded Formulation 5—Novi on Ca Stearate, 0.502%
4. Extruded Formulation 6—Novi sprayed on compounded matrix**, 0.628%

5. Recruit IV PTC bait containing 0.5% noviflumuron
6. Blank PTC Briquettes control
 *=sprayed on cellulose powder, compacted and then broken into prills (granules or pellets)
 **=pre-formed prills (granules or pellets) sprayed on with active Notes: For *C. formosanus*, Formulation 4 was not tested as no more material was available.

For *R. hesperus* & *H. aureus*, only Formulations 1, 2 and 5 were tested due to low termite availability.

Feeding response data for species *R. Virginicus* are set forth in Table 12 below:

TABLE 12

Study 1: Continuous Force-Feeding (No-Choice) Exposure/Efficacy Test. Feeding Response of *R. virginicus* to Extruded Bait Matrix Formulations containing Noviflumuron after 28, 42 and 56 days.

| Treatment | mg consumed after 28 days (mean ± SEM)* | mg consumed after 42 days (mean ± SEM)* | mg consumed after 56 days (mean ± SEM)* |
|---|---|---|---|
| Extruded Formulation 1 (Blank) | 70.93 ± 12.3 a | 122.94 ± 6.8 a | 108.63 ± 22.9 a |
| Extruded Formulation 4 (0.774% Novi on fiber) | 40.04 ± 14.6 bc | 53.32 ± 10.7 ab | 46.28 ± 10.9 bc |
| Extruded Formulation 5 (0.502% Novi in Ca Stearate) | 48.63 ± 12.1 ab | 80.82 ± 12.4 a | 65.37 ± 13.1 b |
| Extruded Formulation 6 (0.628% Novi sprayed on compounded matrix) | 33.76 ± 12.4 bc | 58.35 ± 9.9 c | 40.95 ± 14.2 bc |
| Recruit IV PTC (0.5% Novi) | 16.19 ± 1.7 c | 19.4 ± 1.9 b | 15.69 ± 2.65 c |
| Blank PTC Briquettes | 68.15 ± 8.4 a | 77.85 ± 14.2 a | 54.17 ± 11.4 b |

Figure 10:
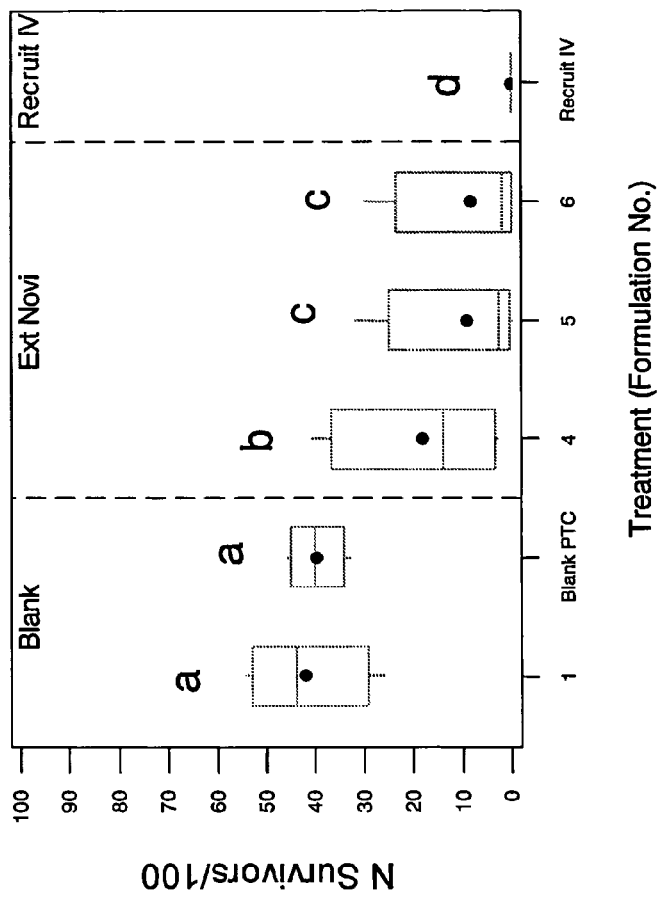
FIG. 10 is a chart depicting survivorship data from the experiment reported in Example 7.
Figure 11:
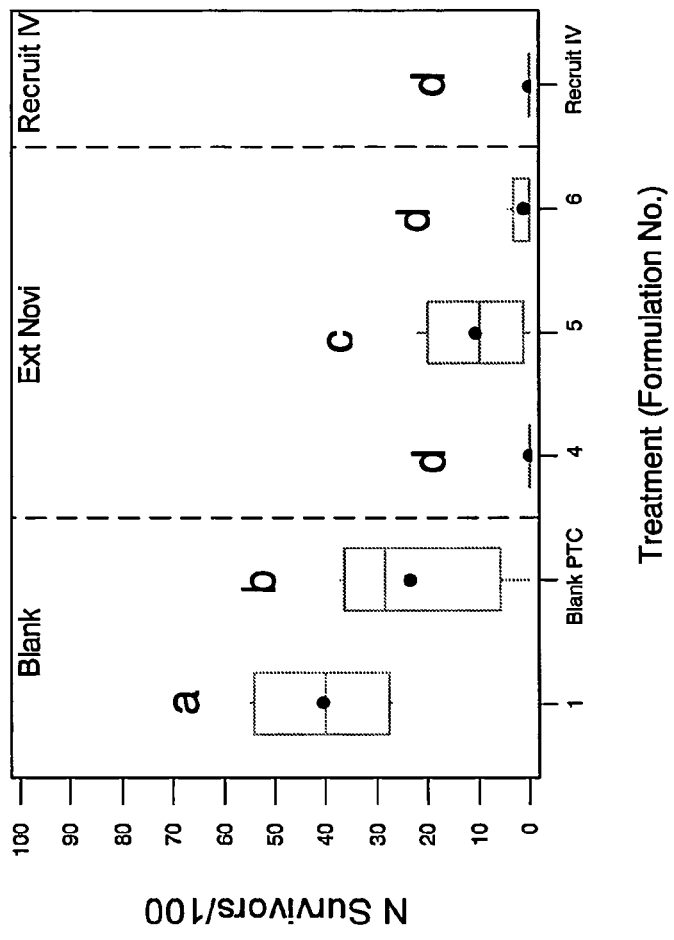
FIG. 11 is a chart depicting survivorship data from the experiment reported in Example 7.
Figure 12:
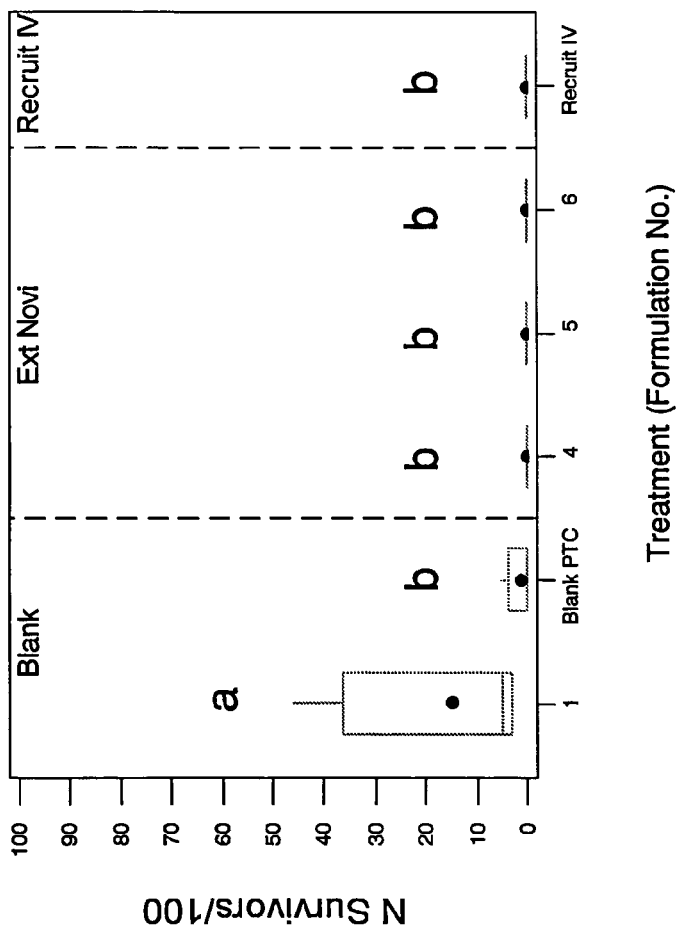
FIG. 12 is a chart depicting survivorship data from the experiment reported in Example 7.

Each treatment replicated 4 times (100 termites per rep).
*Within each columns, means followed by same letter are not significantly different (ANOVA + LSD; p > 0.10).
28, 42, and 56 day readings from 3 separate tests. SEM = Standard Error of the Mean Survivorship data at 4 weeks, 6 weeks and 8 weeks for *R. Virginicus* are set forth in FIGS. 10, 11 and 12, respectively.

Feeding response data for species *C. formosanus* are set forth in Table 13 below:

TABLE 13

Study 1: Continuous Force-Feeding (No-Choice) Exposure/Efficacy Test. Feeding Response of *C. formosanus* to Extruded Bait Matrix Formulations containing Noviflumuron after 28, 42 and 56 days.

| Treatment | mg consumed after 28 days (mean ± SEM)* | mg consumed after 42 days (mean ± SEM)* | mg consumed after 56 days (mean ± SEM)* |
|---|---|---|---|
| Extruded Formulation 1 (Blank) | 102.33 ± 9.88 a | 114.04 ± 38.2 a | 173.37 ± 69.4 a |
| Extruded Formulation 4 (0.774% Novi on fiber) | 60.64 ± 5.11 c | 71.49 ± 4.23 ab | 31.31 ± 28.1 c |
| Extruded Formulation 5 (0.502% Novi in Ca Stearate) | 83.94 ± 5.02 ab | 113.81 ± 6.8 a | 125.22 ± 35.6 b |
| Recruit IV PTC (0.5% Novi) | 27.36 ± 2.03 d | 30.85 ± 2.92 b | 27.93 ± 14.2 c |
| Blank PTC Briquettes | 63.70 ± 15.9 bc | 94.85 ± 1.97 a | 96.95 ± 55.9 b |

Figure 13:
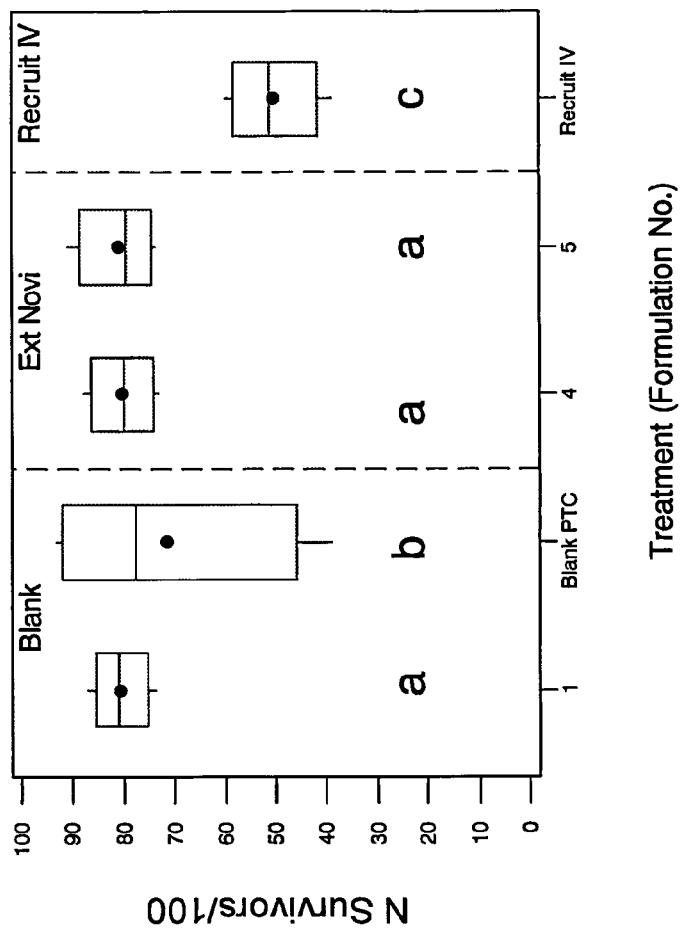
FIG. 13 is a chart depicting survivorship data from the experiment reported in Example 7.
Figure 14:
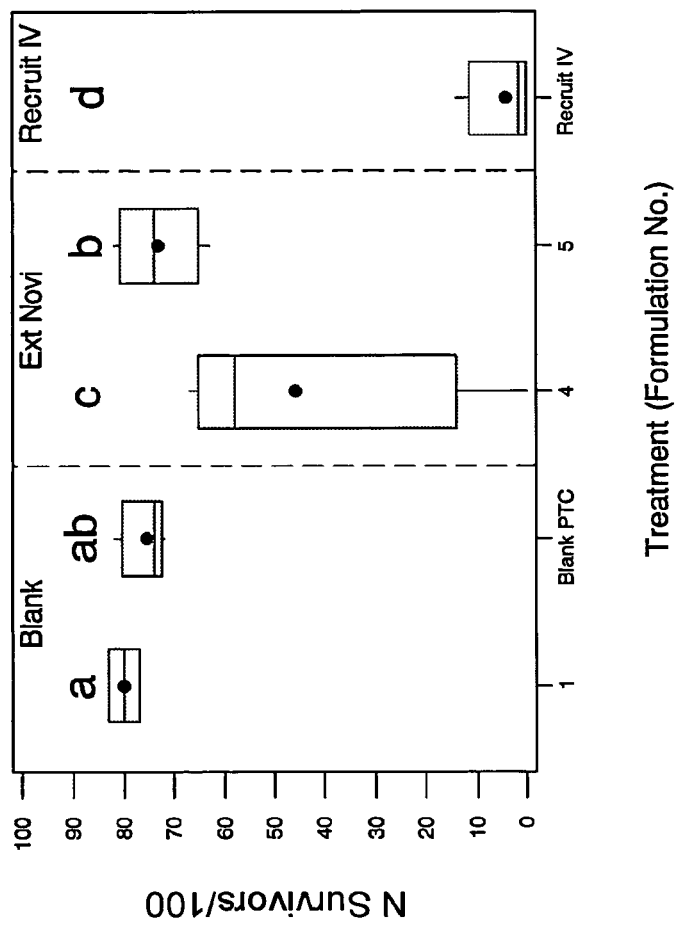
FIG. 14 is a chart depicting survivorship data from the experiment reported in Example 7.
Figure 15:
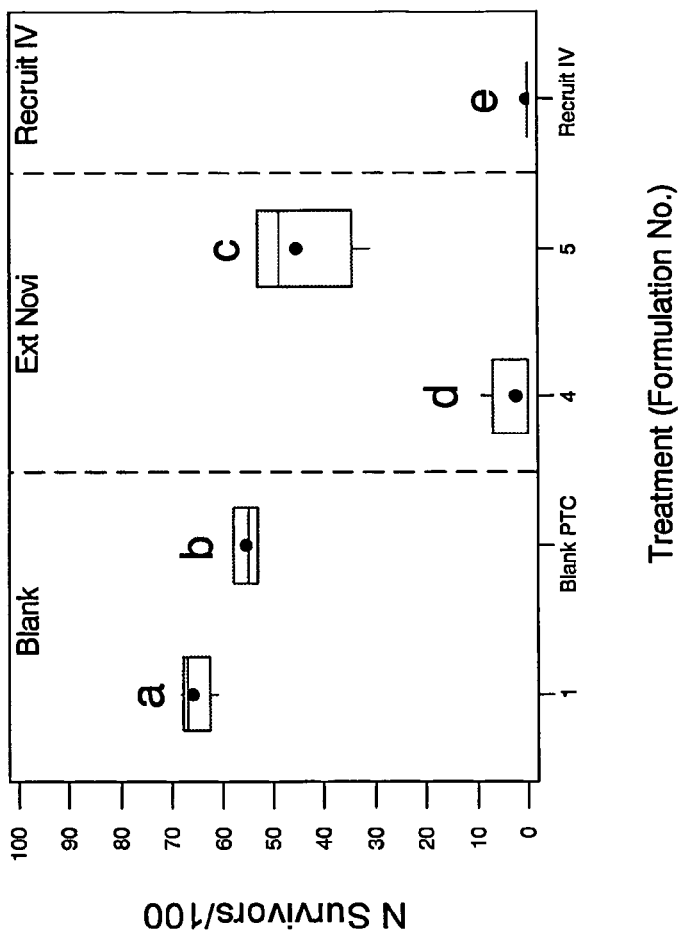
FIG. 15 is a chart depicting survivorship data from the experiment reported in Example 7.

Each treatment replicated 4 times (100 termites per rep).
*Within each columns, means followed by same letter are not significantly different (ANOVA + LSD; p > 0.10).
28, 42, and 56 d readings from 3 separate tests. SEM = Standard Error of the Mean Survivorship data at 4 weeks, 6 weeks and 8 weeks for *C. formosanus* are set forth in FIGS. 13, 14 and 15, respectively.

Feeding response data for species *Heterotermes aureus* are set forth in Table 14 below:

TABLE 14

Study 1: Continuous Force-Feeding (No-Choice) Exposure/Efficacy Test. Feeding Response of *Heterotermes aureus* to Extruded Bait Matrix Formulations containing Noviflumuron after 42 days.

| Treatment | mg consumed after 42 days (mean ± SEM)* |
|---|---|
| Extruded Formulation 1 (Blank) | 60.40 ± 7.1 a |
| Extruded #4 (Novi on fiber, 0.774%) | 15.07 ± 3.2 b |
| Recruit IV PTC (0.5% Novi) | 3.96 ± 0.75 c |

Figure 16:
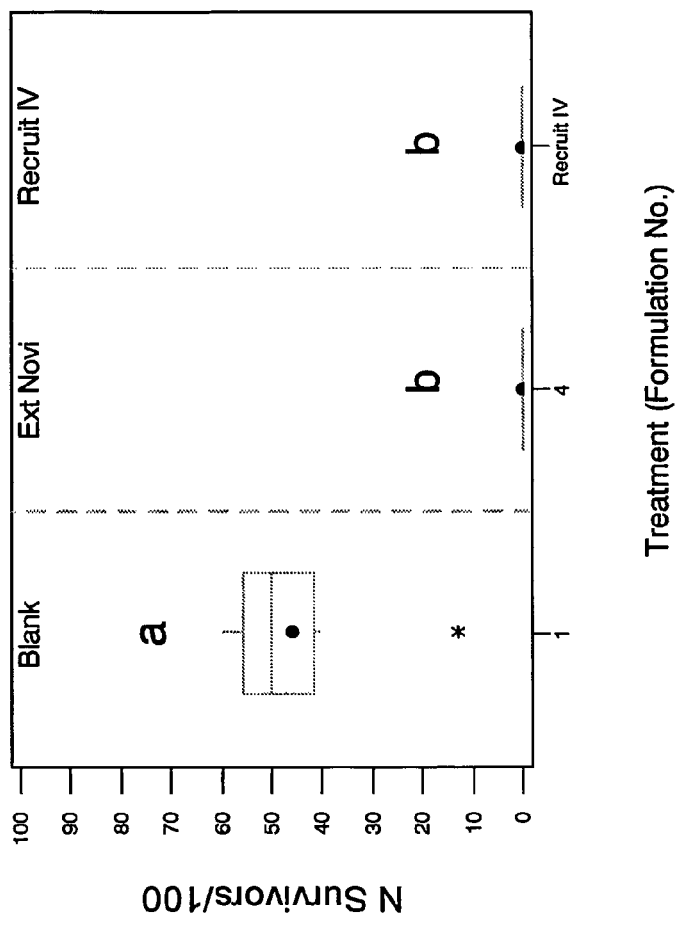
FIG. 16 is a chart depicting survivorship data from the experiment reported in Example 7.

Each treatment replicated 8 times (100 termites per rep).
*Within column, means followed by same letter are not significantly different (ANOVA + LSD; p > 0.10). SEM = Standard Error of the Mean Survivorship data at 6 weeks for *Heterotermes aureus* are set forth in FIG. 16.

Feeding response data for species *Reticulitermes hesperus* are set forth in Table 15 below:

TABLE 15

Study 1: Continuous Force-Feeding (No-Choice) Exposure/Efficacy Test. Feeding Response of *Reticulitermes hesperus* to Extruded Bait Matrix Formulations containing Noviflumuron after 42 days (6 weeks).

| Treatment | mg consumed after 42 days (mean ± SEM)* |
|---|---|
| Extruded Formulation 1 (Blank) | 136.67 ± 15.4 a |
| Extruded Formulation 4 (Novi on fiber, 0.774%) | 36.42 ± 10.0 b |
| Recruit IV PTC (0.5% Novi) | 14.69 ± 4.06 c |

Figure 17:
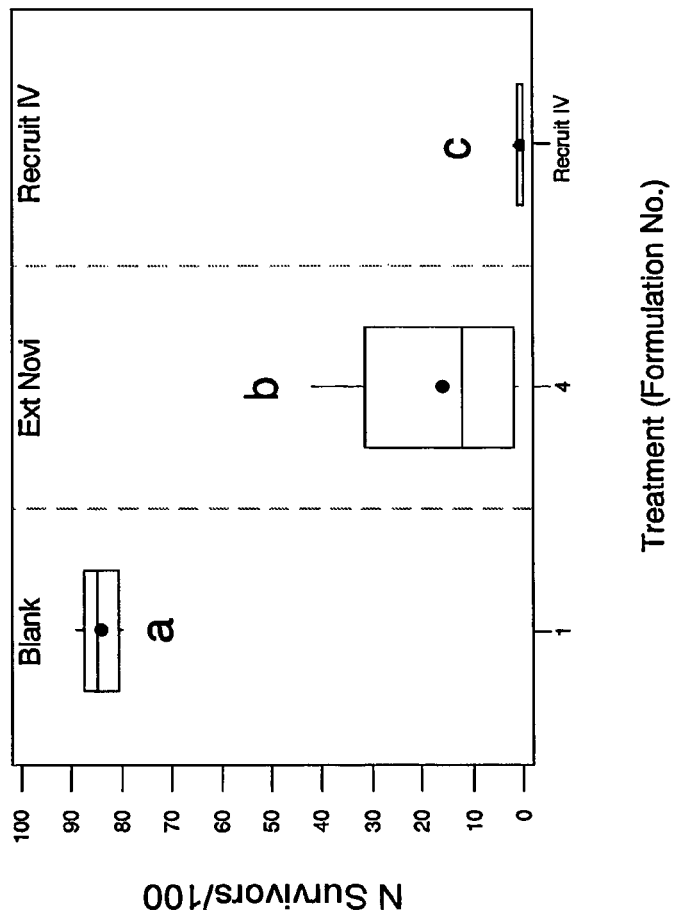
FIG. 17 is a chart depicting survivorship data from the experiment reported in Example 7.

Each treatment replicated 8 times (100 termites per rep).
*Within this column, means followed by same letter are not significantly different (ANOVA + LSD; p > 0.10). SEM = Standard Error of the Mean Survivorship data at 6 weeks for *Reticulitermes hesperus* are set forth in FIG. 17.

In addition to the above, similar tests were conducted in Japan to test the consumption and efficacy of noviflumuron-containing extruded composite materials to subterranean termite species *R. speratus*. Results of these tests (data not shown) revealed that *R. speratus* consumed more extruded composite material compared to Recruit IV in the no-choice lab tests at 4 weeks and 6 weeks and that the number of survivors after exposure to the noviflumuron-containing extruded composite material was greater than that of Recruit IV, but less than controls.

Study #2: Consumption & Efficacy of Extruded Hexaflumuron Formulations to Additional Termite Species
Species: *R. virginicus, C. formosanus, R. hesperus, H. aureus*
Test Set-up: One-way, continuous no-choice tests, 4-7 reps, 100 termites per rep, 6 and/or 10-week data (*C. formosanus* only)
Treatments
1. Extruded Formulation 1—Blank
2. Extruded Formulation 2*—0.78% Hex on Fiber
3. Extruded Formulation 3—0.475% Hex in Ca Stearate
4. Shatter bait containing 0.5% Hexaflumuron
5. Blank PTC pellets control
 *=sprayed on cellulose powder, compacted and then broken into prills (granules or pellets)
Notes: For *R. hesperus* & *H. aureus*, only Formulations 1, 2 and 4 were tested due to low termite availability.

Feeding response data for species *Reticulitermes virginicus* are set forth in Table 16 below:

TABLE 16

Study 2: Continuous Force-Feeding (No-Choice) Exposure/Efficacy Test. Feeding Response of *Reticulitermes virginicus* to Extruded Bait Matrix Formulations containing Hexaflumuron after 42 days (6 weeks).

| Treatment | mg consumed after 10 weeks (mean ± SEM)* |
|---|---|
| Extruded Formulation 1 (Blank) | 99.43 ± 17.0 a |
| Extruded Formulation 2 (Hex on fiber, 0.78%) | 81.01 ± 7.93 b |
| Extruded Formulation 3 (Hex in Ca Stearate, 0.475%) | 76.50 ± 6.09 a |
| Blank PTC | 67.57 ± 17.8 a |
| Shatter | 46.29 ± 3.60 a |

Figure 18:
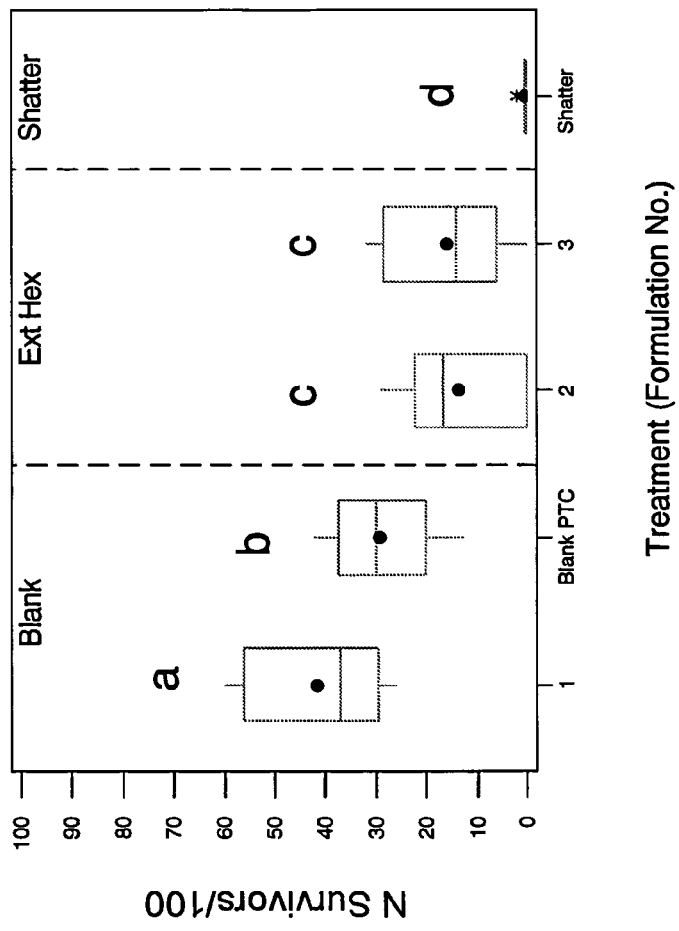
FIG. 18 is a chart depicting survivorship data from the experiment reported in Example 7.

Each treatment replicated 6 times (100 termites per rep).
*Within this column, means followed by same letter are not significantly different (ANOVA + LSD; p > 0.10). SEM = Standard Error of the Mean Survivorship data at 6 weeks for *Reticulitermes virginicus* are set forth in FIG. 18.

Feeding response data for species *Coptotermes formosanus* are set forth in Table 17 below:

TABLE 17

Study 2: Continuous Force-Feeding (No-Choice) Exposure/Efficacy Test. Feeding Response of *Coptotermes formosanus* to Extruded Bait Matrix Formulations containing Hexaflumuron after 10 weeks.

| Treatment | mg consumed after 10 weeks (mean ± SEM)* |
|---|---|
| Extruded Formulation 1 (Blank) | 194.24 ± 10.1 a |
| Extruded Formulation 2 (Hex on fiber, 0.78%) | 147.61 ± 8.01 b |
| Extruded Formulation 3 (Hex in Ca Stearate, 0.475%) | 185.90 ± 9.37 a |

Figure 19:
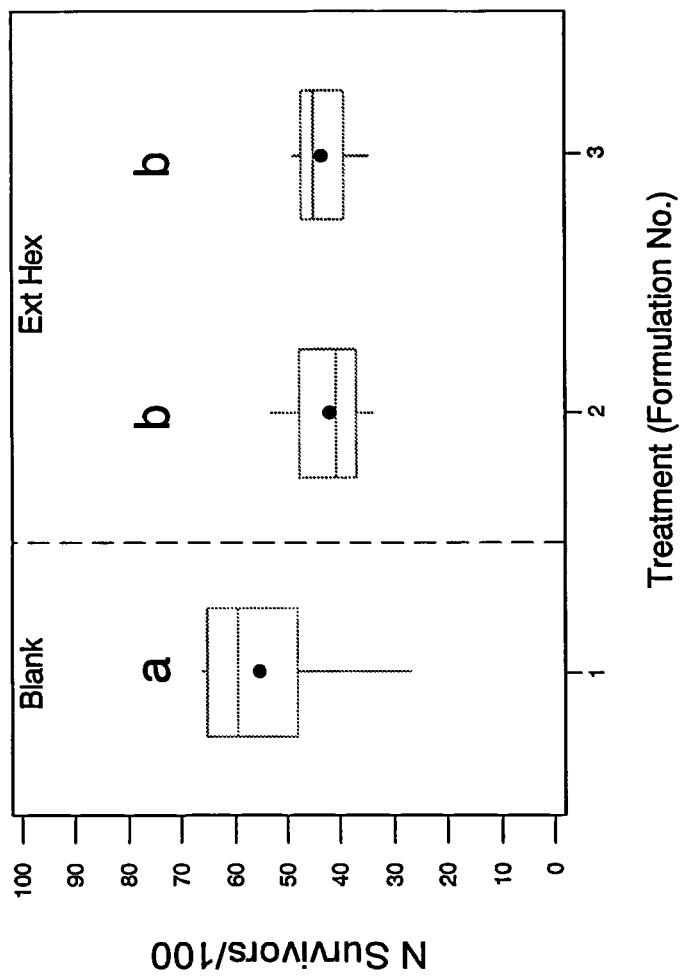
FIG. 19 is a chart depicting survivorship data from the experiment reported in Example 7.

Each treatment replicated 6 times (100 termites per rep).
*Within this column, means followed by same letter are not significantly different (ANOVA + LSD; p > 0.10). SEM = Standard Error of the Mean Survivorship data at 10 weeks for *Coptotermes formosanus* are set forth in FIG. 19.

Feeding response data for species *Heterotermes aureus* are set forth in Table 18 below:

TABLE 18

Study 2: Continuous Force-Feeding (No-Choice) Exposure/Efficacy Test. Feeding Response of *Heterotermes aureus* to Extruded Bait Matrix Formulations containing Hexaflumuron after 45 days (6+ weeks).

| Treatment | mg consumed after 10 weeks (mean ± SEM)* |
|---|---|
| Extruded Formulation 1 (Blank) | 44.27 ± 10.7 a |
| Extruded Formulation 2 (Hex on fiber, 0.78%) | 35.65 ± 7.75 a |
| Shatter (0.5% Hexaflumuron) | 32.26 ± 4.06 a |

Figure 20:
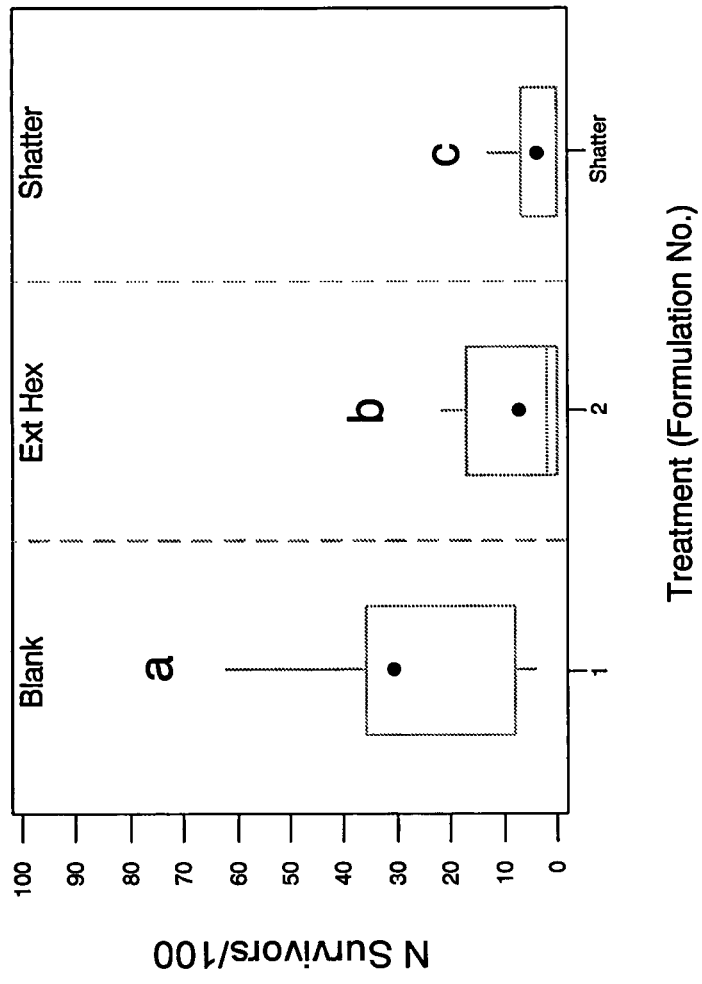
FIG. 20 is a chart depicting survivorship data from the experiment reported in Example 7.

Each treatment replicated 7 times (100 termites per rep).
*Within this column, means followed by same letter are not significantly different (ANOVA + LSD; p > 0.10). SEM = Standard Error of the Mean Survivorship data at 45 days for *Heterotermes aureus* are set forth in FIG. 20.

Feeding response data for species *Reticulitermes hesperus* are set forth in Table 19 below:

TABLE 19

Study 2: Continuous Force-Feeding (No-Choice) Exposure/Efficacy Test. Feeding Response of *Reticulitermes hesperus* to Extruded Bait Matrix Formulations containing Hexaflumuron after 42-d (6 weeks).

| Treatment | mg consumed after 10 weeks (mean ± SEM)* |
|---|---|
| Extruded Formulation 1 (Blank) | 82.17 ± 16.2 a |
| Extruded Formulation 2 (Hex on fiber, 0.78%) | 53.76 ± 14.9 b |
| Shatter (0.5% Hexaflumuron) | 62.88 ± 16.7 b |

Figure 21:
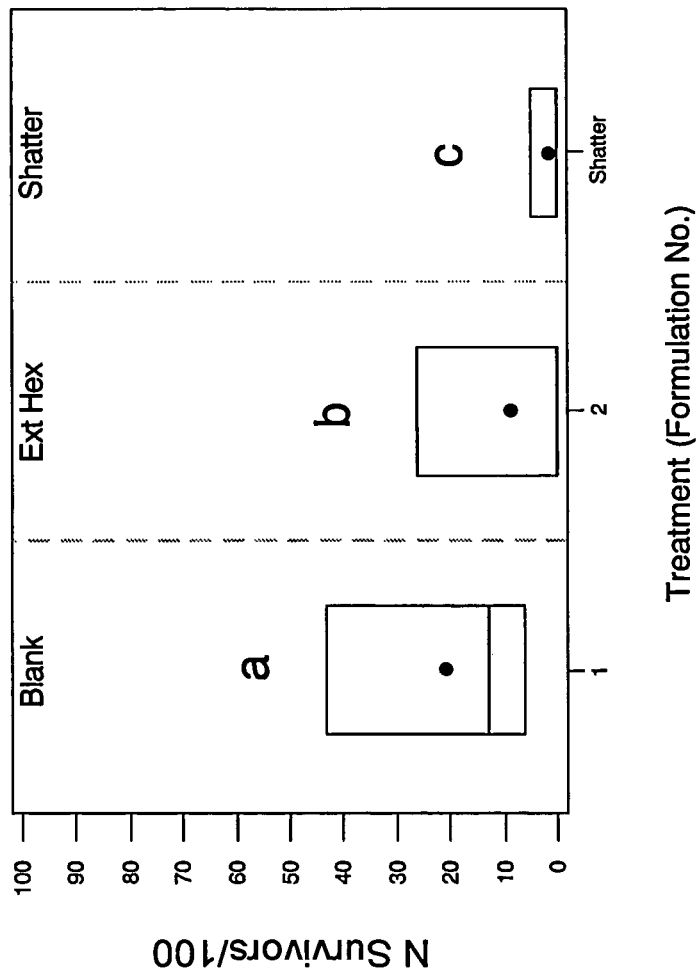
FIG. 21 is a chart depicting survivorship data from the experiment reported in Example 7.

Each treatment replicated 7 times (100 termites per rep).
*Within this column, means followed by same letter are not significantly differeant (ANOVA + LSD; p > 0.10). SEM = Standard Error of the Mean Survivorship data at 6 weeks for *Reticulitermes hesperus* are set forth in FIG. 21.

As shown by the data set forth above, key subterranean termite species *R. virginicus, C. formosanus, R. hesperus* and *H. aureus* consume (mg) more (p=0.1) of the extruded formulations containing noviflumuron and compared to Recruit IV in no-choice laboratory tests at 4, 6 and 8 weeks, and subterranean termite species *R. virginicus, C. formosanus, R. hesperus* and *H. aureus* consume (mg) more (p=0.1) of the extruded formulations containing hexaflumuron compared to Shatter in no-choice laboratory tests at 6 weeks. While composite materials containing noviflumuron generally cause less mortality vs. Recruit IV to the subterranean termite species tested in no-choice laboratory tests at 4, 6 and 8 weeks, the composite materials containing noviflumuron did cause more mortality than controls, indicating that the extruded composite materials are an effective manner of delivering this AI to termites. Extruded composite materials containing hexaflumuron caused similar levels of mortality vs. Shatter (p=0.05, Binary Logistic Regression) to some of the subterranean termite species tested in no-choice laboratory tests at 6 weeks. While the extruded composite materials containing hexaflumuron caused less mortality than Shatter to other termite species, the hexaflumuron-containing extruded composite materials did cause higher levels of mortality than controls to these species, indicating that the extruded composite materials are an effective manner of delivering this AI to termites.

Example Eight

Trophallaxis Transfer of Extruded Pesticide Composite Materials

Figure 22:
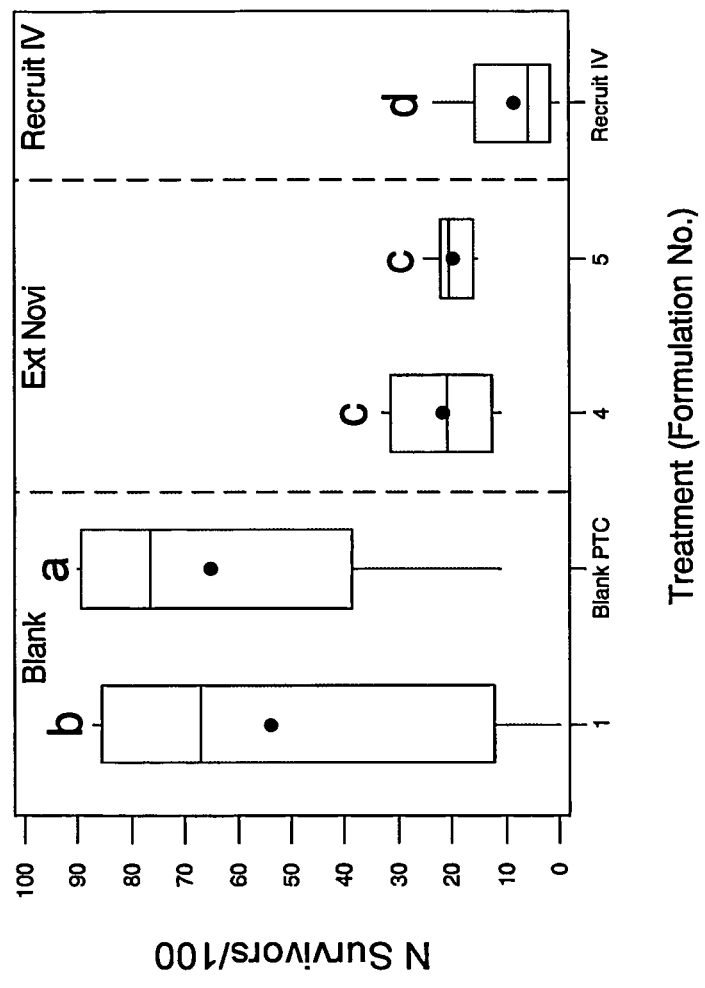
FIG. 22 is a chart depicting trophallaxis transfer survivorship data from the experiment reported in Example 8.
Figure 23:
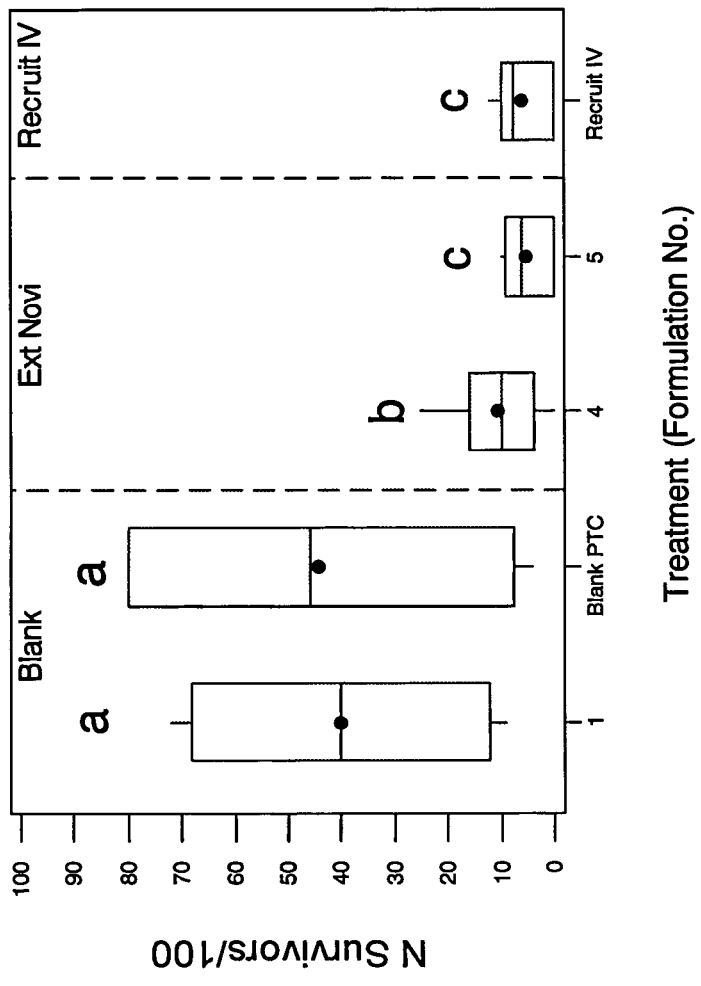
FIG. 23 is a chart depicting trophallaxis transfer survivorship data from the experiment reported in Example 8.
Figure 24:
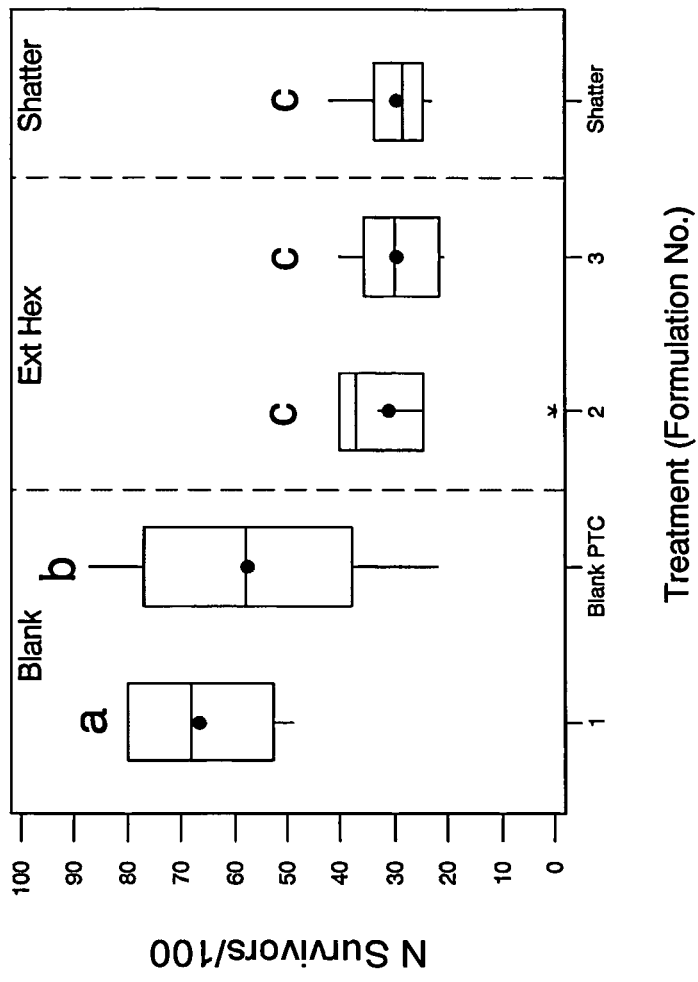
FIG. 24 is a chart depicting trophallaxis transfer survivorship data from the experiment reported in Example 8.
Figure 25:
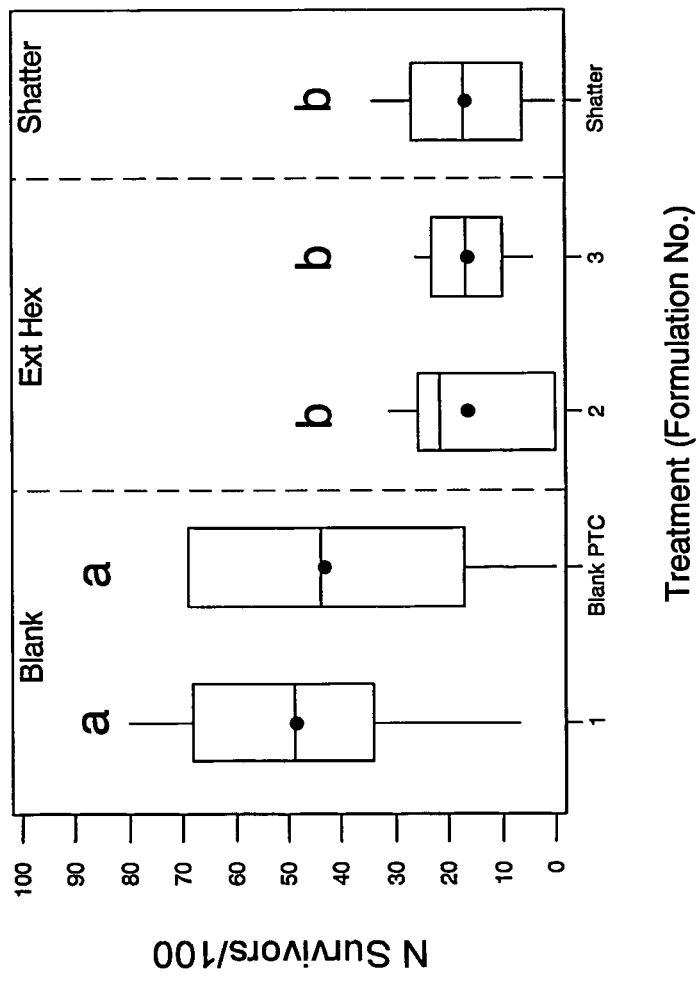
FIG. 25 is a chart depicting trophallaxis transfer survivorship data from the experiment reported in Example 8.

Extruded AI-containing composite materials were compared to commercial AI-containing bait materials to determine if they cause significant mortality to R. favipes in trophallaxis transfer studies at 6 and/or 8 weeks post exposure.
Species: R. favipes
Test Set-up:
Step 1: Exposure to Extruded Material—One-Way Continuous No-Choice Set-Up
6 reps of each treatment per test
Test 1=6 weeks
Test 2=8 weeks
50 termites/rep, and held for 7 days
Step 2: Set-Up of 6 & 8 Week Tests:
From Step 1 take 6 reps/treatment and replace extruded material with 0.5"×1" MD-499 piece.
For each rep/treatment add 50 non-exposed termites (from same colony tub) for 100 termite total/rep.
6 reps, 100 termites/rep, held for 42 days (6 weeks).
Additional 6 reps, 100 termites/rep, held for 56 days (8 weeks).
Treatments:
Noviflumuron Study
1. Extruded Formulation 1—Blank
2. Extruded Formulation 4—Noviflumuron on fiber, Assay=0.774%
3. Extruded Formulation 5—Noviflumuron on Ca Stearate, Assay=0.502%
4. Recruit IV PTC bait containing 0.5% Noviflumuron
5. Blank PTC Briquettes control
Hexaflumuron Study
1. Extruded Formulation 1—Blank
2. Extruded Formulation 2—Hexaflumuron on Fiber, Assay=0.78%
3. Extruded Formulation 3—Hexaflumuron as solid in Ca Stearate, Assay=0.475%
4. Blank PTC Briquettes control
5. Shatter PTC bait containing 0.5% Hexaflumuron The data obtained from the trophallaxis study is set forth in FIGS. 22, 23, 24 and 25, in which FIGS. 22 and 23 are graphs of the number of survivors for each type of material tested in the noviflumuron study at 6 weeks and 8 weeks, respectively, and FIGS. 24 and 25 are graphs of the number of survivors for each type of material tested in the hexaflumuron study at 6 weeks and 8 weeks, respectively. The data set forth in FIGS. 22-25 show that both Noviflumuron and Hexaflumuron 50:50 trophallaxis transfer studies over 7 days and followed out for 6 and 8 weeks had significant mortality in the treatments vs. blanks.

Example Nine

Acceptance and Efficacy of Extruded Pesticidal Composite Materials Including Spinosad and Fipronil Tests were conducted to determine if extruded composite materials including fast-acting AIs (Spinosad and Fipronil) cause significant high mortality vs. control (p=0.05, Binary Logistic Regression) to R. flavipes and C. curvignathus. Extruded materials used in this study were made as described above, with the exception that the AI included in the extrusion was Spinosad or Fipronil as follows: Formulation 10 includes 0.05% Spinosad, Formulation 11 includes 0.01% Fipronil, Formulation 12 includes 0.03% Fipronil, Formulation 13 includes 0.05% Fipronil and Formulation 14 includes 0.1% Fipronil,
Species: R. flavipes and C. curvignathus
R. flavipes (Two Tests)
Test Set-up: Standard One-way no-choice and choice tests (vs, SYP) 6 reps, 100 termites/rep, held for 14 d. Two colonies of R. flavipes used.
Treatments (Both Tests):
1. Extruded Formulation 7 (Blank)
2. Extruded Formulation 10 (0.05% Spinosad)
3. Extruded Formulation 11 (0.01% Fipronil)
4. Extruded Formulation 12 (0.03% Fipronil)
5. Extruded Formulation 13 (0.05% Fipronil)
6. Extruded Formulation 14 (0.1% Fipronil)

Figure 26:
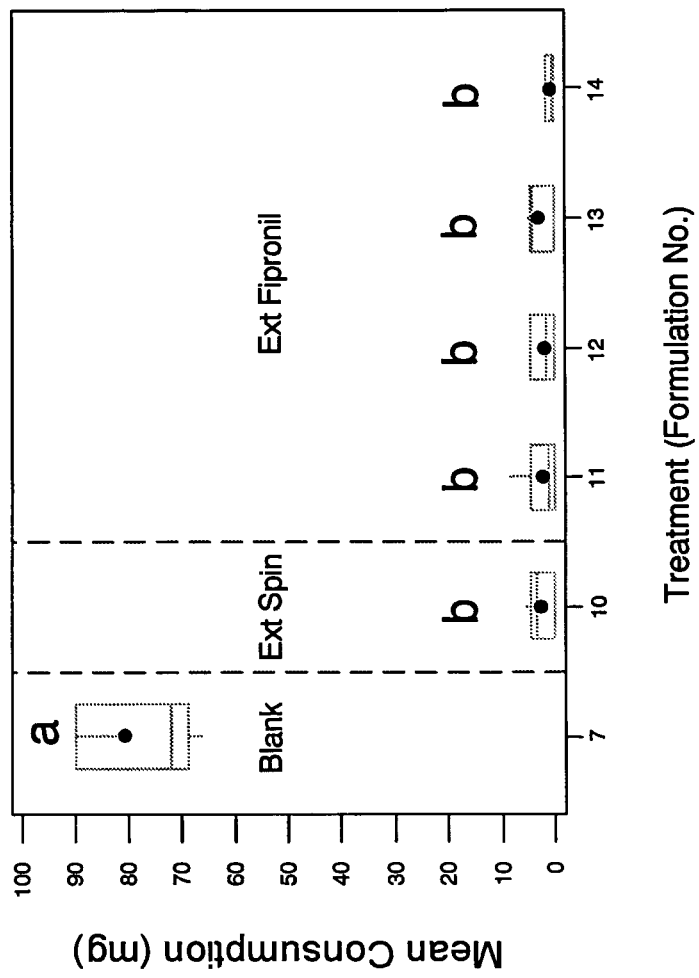
FIG. 26 is a chart depicting consumption data from the experiment reported in Example 9.
Figure 27:
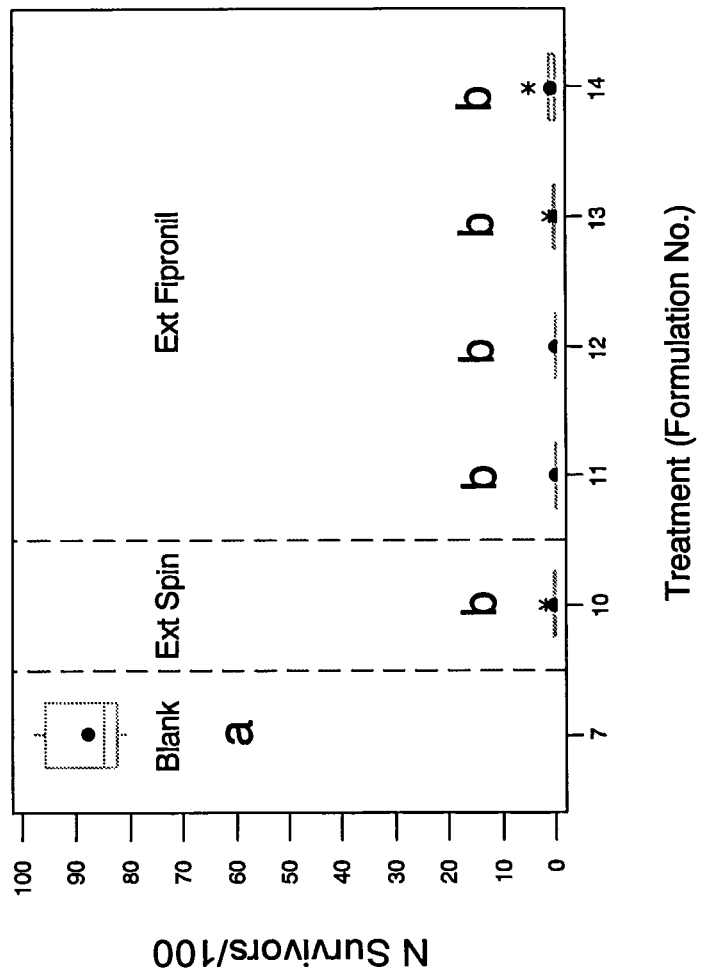
FIG. 27 is a chart depicting survivorship data from the experiment reported in Example 9.
Figure 28:
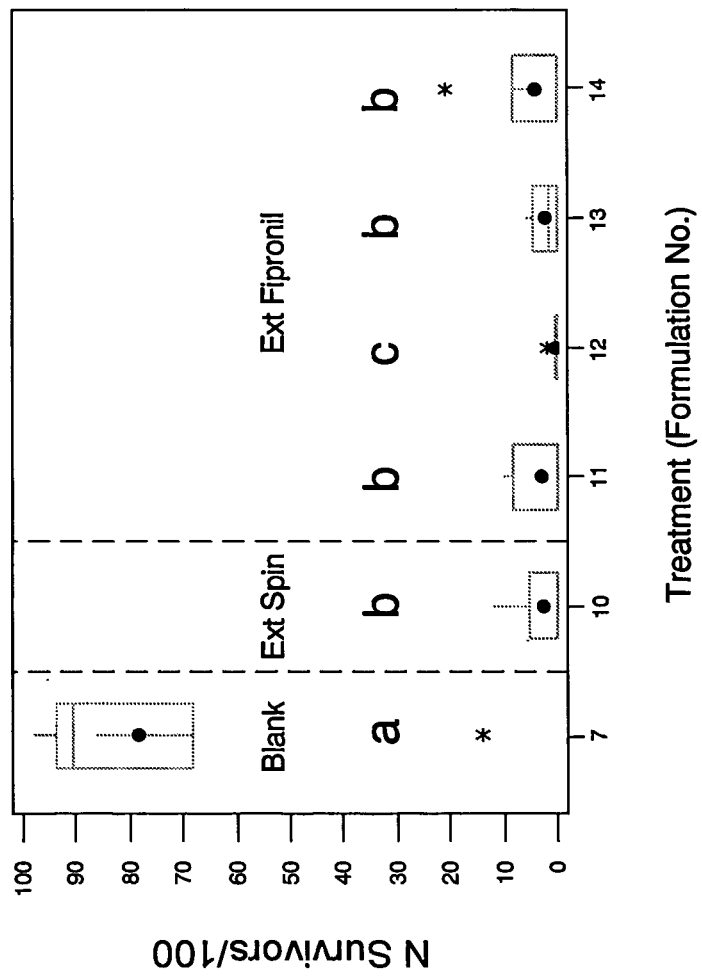
FIG. 28 is a chart depicting survivorship data from the experiment reported in Example 9.

The results of these tests are set forth in FIGS. 26, 27 and 28, in which FIG. 26 sets forth results with respect to consumption of the extruded composite materials by R. Flavipes at 14 days in the no-choice test, FIG. 27 sets forth survivorship results at 14 days in the no-choice test and FIG. 28 sets forth the results of the survivorship test at 14 days in the choice v. SYP test. As shown by these results, extruded composite materials including the fast-acting AIs Spinosad and Fipronil cause significant high mortality vs. control to R. flavipes after two weeks in laboratory choice and no-choice tests.

C. curvignathus Test
Test Set-up: One-way no choice consumption and efficacy, 4 replicates per treatment. Assessment at 7-day post-treatment.
Treatments:
1. Extruded Formulation 10 (0.05% spinosad)
2. Extruded Formulation 11 (0.01% fipronil)
3. Extruded Formulation 12 (0.03% fipronil)
4. Extruded Formulation 13 (0.05% fipronil)
5. Extruded Formulation 14 (0.1% fipronil)

Extruded bait consumption data of C. curvignathus after 7 days is provided below in Table 20.

TABLE 20

| Treatment | Mean ± S.D. (mg) |
| --- | --- |
| Rubber wood (untreated) | 11.65 ± 12.42 |
| Formulation 10 (0.05% spinosad) | 2.58 ± 1.10 |
| Formulation 11 (0.01% fipronil) | 6.75 ± 6.83 |
| Formulation 12 (0.03% fipronil) | 3.88 ± 6.17 |
| Formulation 13 (0.05% fipronil) | 4.28 ± 11.55 |
| Formulation 14 (0.1% fipronil) | 5.63 ± 6.35 |

Percent survival data of the worker termite of *C. curvignathus* at 7 days is provided below in Table 21.

TABLE 21

| Treatment | Mean (%) |
|---|---|
| Rubber wood (untreated) | 100 |
| Formulation 10 (0.05% spinosad) | 46.5 |
| Formulation 11 (0.01% fipronil) | 0 |
| Formulation 12 (0.03% fipronil) | 0 |
| Formulation 13 (0.05% fipronil) | 0 |
| Formulation 14 (0.1% fipronil) | 25.5 |

Mortality is achieved mostly within 1-2 days upon introduction of bait. Spinosad bait is the only treatment where some sand/vermiculite particles were observed at the foraging chamber, and some termite refused to cross over to the foraging chamber, possibly indicating possibly some deterrence. All termite were killed in the chamber containing fipronil bait (Formulation 11, Formulation 12 & Formulation 13) except Formulation 14 (25% survivorship). As seen from the above, extruded composite materials including the fast acting AIs Spinosad and Fipronil cause high mortality vs. control to *C. curvignathus* after one week in the laboratory no-choice test.

Example Ten

Termite Colony Elimination Study

Field tests were performed to determine if extruded noviflumuron and/or hexaflumuron bait matrix eliminate subterranean termite colonies when placed in active in-ground SENTRICON® stations, and to determine the amount of time and quantity of bait consumption needed to effect colony elimination. Extruded materials used in this study were made as described above and provided in the form of rods each having a mass of about 75 grams. The materials used in this test are the following: Formulation 15 rods include 0.58% Hexaflumuron and Formulation 16 rods include 0.78% Noviflumuron.

Test Set-up: Termite colonies were exposed to AI-containing extruded composite material rods having a mass of about 75 grams. As a point of reference, Recruit IV bait tubes have a mass of about 65 grams.

Termite species tested: *R. flavipes* (RETIFL), *R. hageni* (RETIHA), *C. formosanus* (COPTFO), *R. virginicus* (RETIVI) and *R. Hesperus* (RETIHE).

Treatments:

1. Formulation 15  0.58% Hexaflumuron Rods (extruded bait matrix)
2. Formulation 16  0.78% Noviflumuron Rods (extruded bait matrix)

Figure 29:
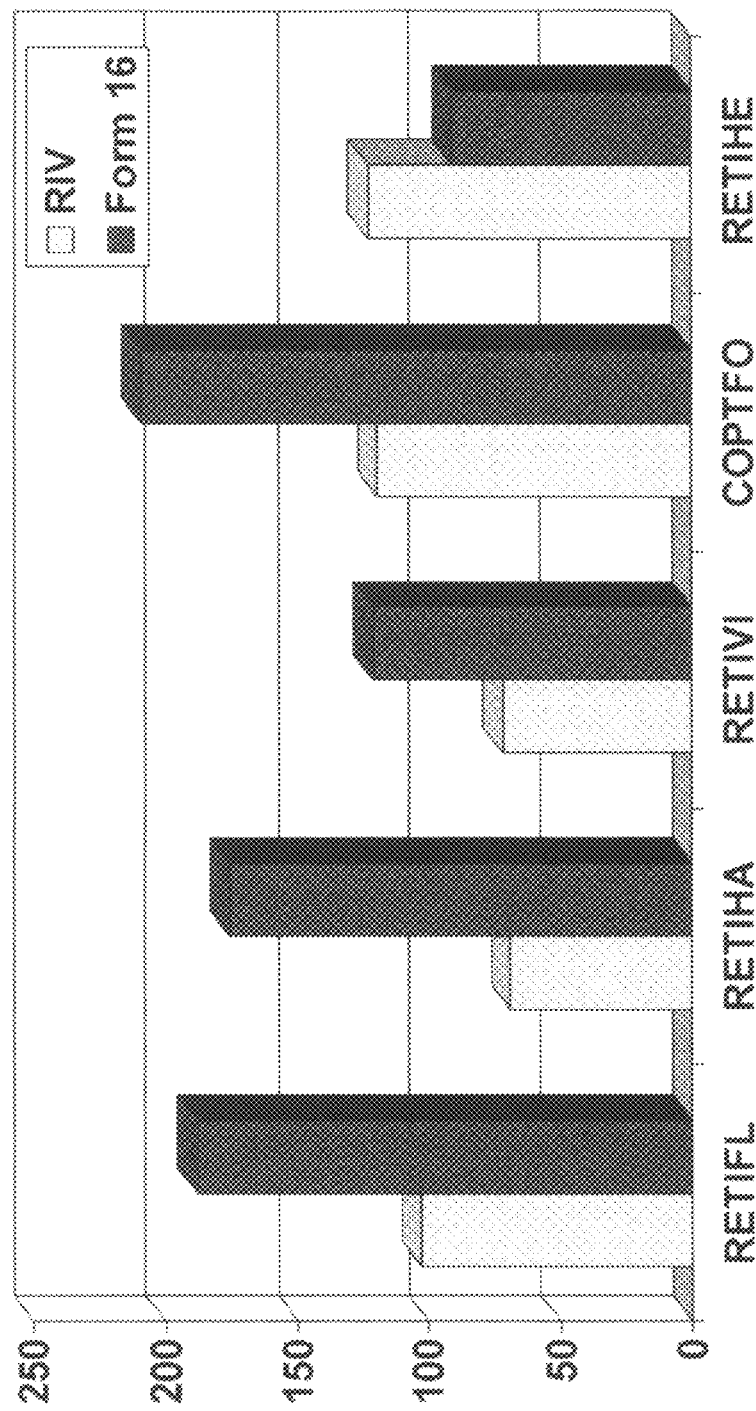
FIG. 29 is a chart depicting mean days to elimination data from the experiment reported in Example 10.
Figure 30:
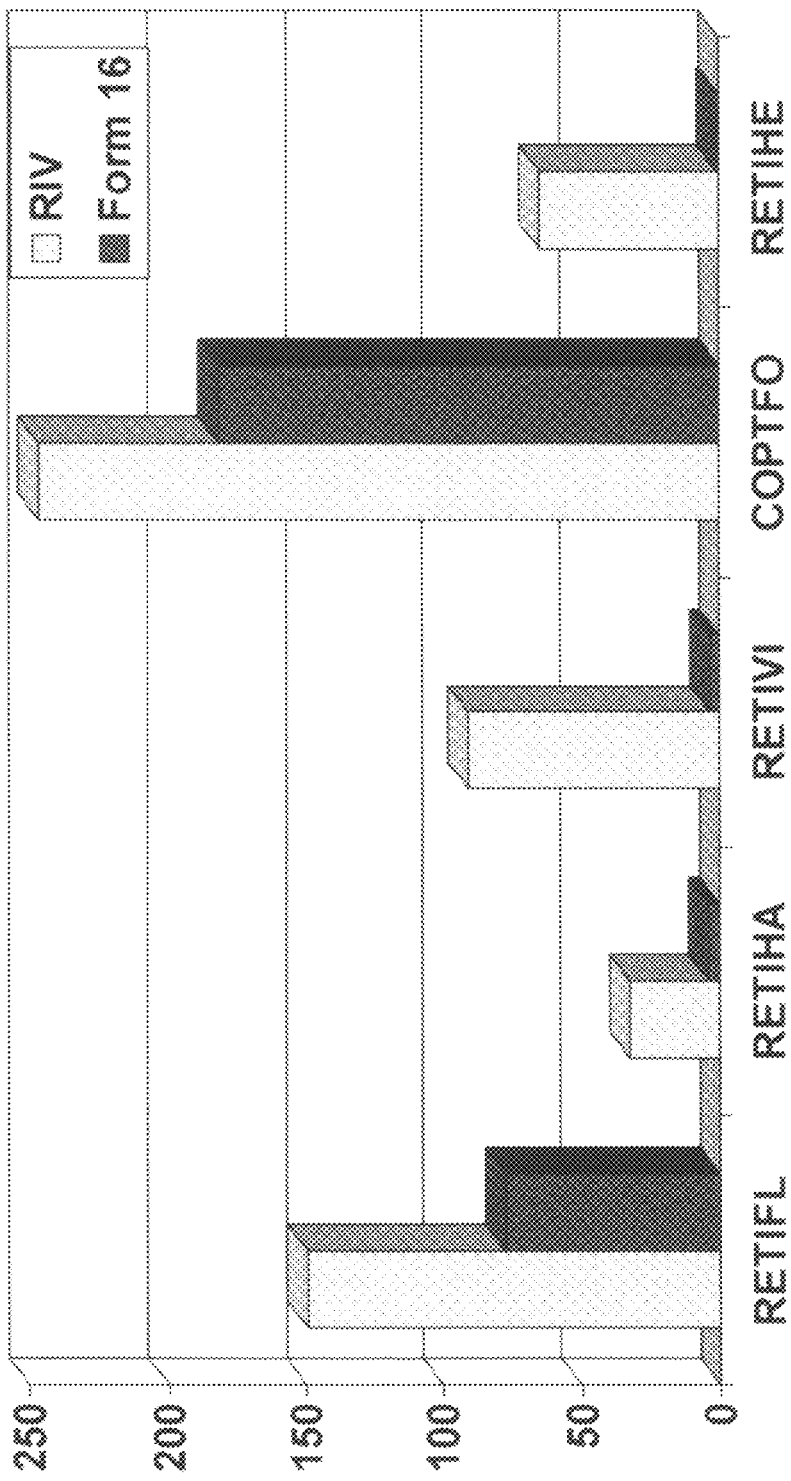
FIG. 30 is a chart depicting consumption data from the experiment reported in Example 10.
Figure 31:
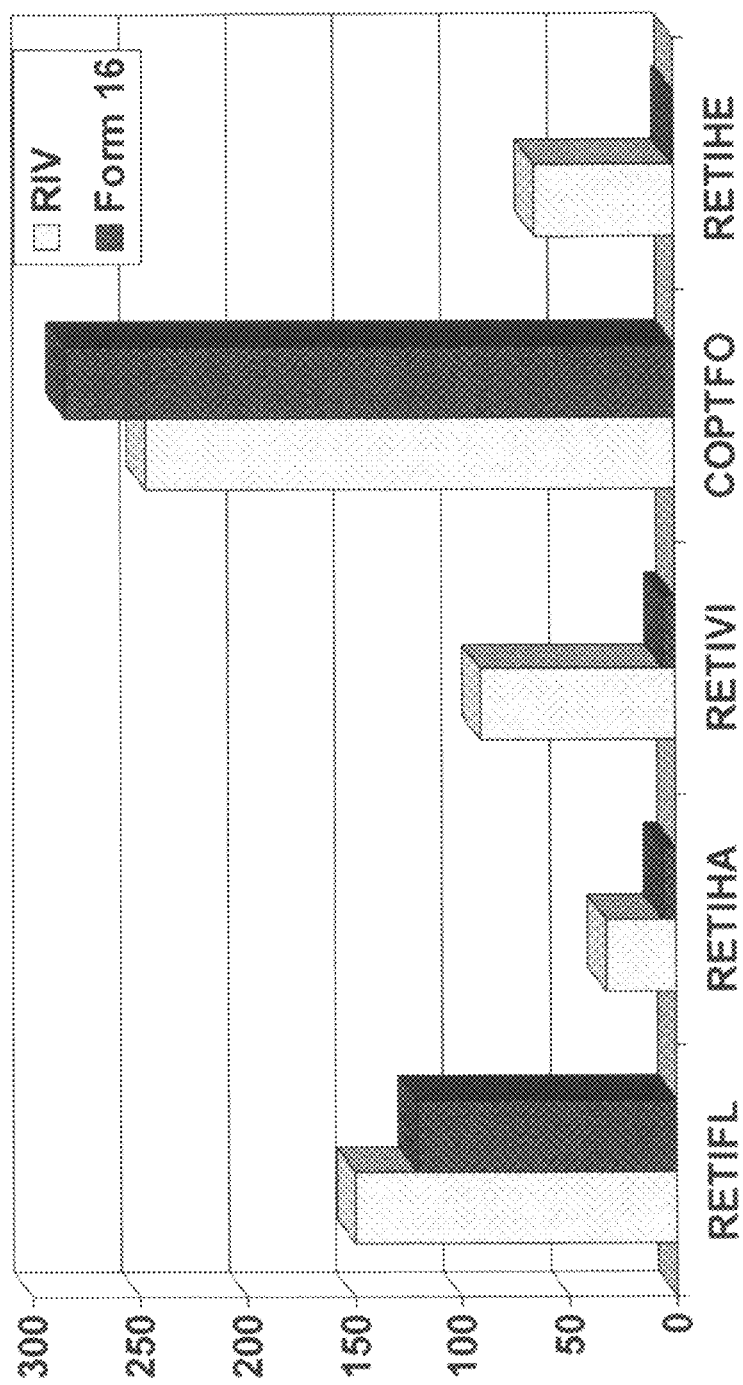
FIG. 31 is a chart depicting consumption data from the experiment reported in Example 10.

Results/Discussion:

Table 22 sets forth data regarding each of the 15 elimination trials, including the U.S. State in which the trial was performed, the termite species tested, the Formulation tested, the amount consumed (number of rods) and the number of days to elimination of the colony. In addition, comparisons to elimination data for Recruit IV are provided in FIGS. 29, 30 and 31, in which FIG. 29 compares mean days to elimination between Recruit IV (RIV) and Formulation 16, FIG. 30 compares mean grams of bait consumed to elimination between Recruit IV (RIV) and Formulation 16, and FIG. 31 compares mean grams of bait consumed to elimination adjusted for percent AI in the AI-containing extruded composite matrix between Recruit IV (RIV) and Formulation 16.

TABLE 22

| Trial # | Location | Species | Formul. | Consumed (# of rods) | Days to elimination |
|---|---|---|---|---|---|
| 1 | FL | R. flavipes | Formulation 16 | 0.70 | 120 |
| 2 | FL | R. hageni | Formulation 16 | 0.07 | 198 |
| 3 | FL | R. hageni | Formulation 16 | 0.05 | 198 |
| 4 | FL | R. hageni | Formulation 16 | 0.04 | 142 |
| 5 | FL | R. hageni | Formulation 15 | 0.04 | 142 |
| 6 | FL | R. hageni | Formulation 15 | 0.30 | 198 |
| 7 | FL | R. hageni | Formulation 16 | 0.06 | 142 |
| 8 | FL | R. hageni | Formulation 16 | NA | NA |
| 9 | FL | R. hageni | Formulation 16 | 0.05 | 120 |
| 10 | LA | C. formosanus | Formulation 16 | 2.6 | 209 |
| 11 | MS | R. flavipes | Formulation 16 | 0.31 | 166 |
| 12 | MS | R. flavipes | Formulation 16 | 0.21 | 121 |
| 13 | IN | R. flavipes | Formulation 16 | 3.20 | 343 |
| 14 | MS | R. virginicus | Formulation 16 | 0.05 | 121 |
| 15 | CA | R. Hesperus | Formulation 16 | 0.01 | 121 |

The data set forth above show that the AI-containing extruded composite materials did eliminate termite colonies. Average days to elimination across all trials was 188 and the maximum was 343, both within desired parameters. The quantity of bait consumed averaged 0.37 rods with a maximum of 2.6 rods. Consumption of AI was roughly equivalent for *R. flavipes* and *C. formosanus*, but greatly reduced for other species. These trials were initiated in late fall/winter, so the results are worst case.

While multiple embodiments have been illustrated and described in detail in the drawings and foregoing description, the same is to be considered illustrative and not restrictive in character, it being understood that only selected embodiments have been shown and described and that all changes, equivalents, and modifications as would occur to those skilled in the art and that come within the scope of the inventions described herein or defined by the following claims are desired to be protected. Any theory, mechanism of operation, proof, or finding stated herein is meant to further enhance understanding of the present application and is not intended to limit the inventions in any way to such theory, mechanism of operation, proof, or finding. In addition, the various procedures, techniques, and operations may be altered, rearranged, substituted, deleted, duplicated, or combined as would occur to those skilled in the art. Further, any U.S. Patent, pending U.S. Patent Application Publication or other publication cited herein is incorporated herein by reference in its entirety as if each individual publication, patent, or patent application was specifically and individually indicated to be incorporated by reference and set forth in its entirety herein, including but not limited to, International Patent Application Number PCT/US03/08690, filed 21 Mar. 2003, U.S. Pat. No. 7,212,129 filed 21 Mar. 2002, U.S. Pat. No. 7,262,702 filed 9 Aug. 2001, International Patent Application Number PCT/US00/26373 filed 25 Sep. 2000, International Patent Application Number PCT/US99/16519 filed 21 Jul. 1999, U.S. Pat. No. 6,724,312 filed 25 Sep. 2000, and U.S. Published Patent Application No. 2001/0033230 filed 20 Mar. 2001. In reading the claims, words such as the word "a," the word "an," the words "at least one," and the words "at least a portion" are not intended to limit the claims to only one item unless specifically stated to the contrary. Further, when the language "at least a portion" and/or "a portion" is used, the claims may include a portion and/or the entire item unless specifically stated to the contrary.

Any reference to a specific direction, for example, references to up, upper, down, lower, and the like, is to be understood for illustrative purposes only or to better identify or distinguish various components from one another. Unless specifically identified to the contrary, all terms used herein are used to include their normal and customary terminology. Further, while various embodiments of insect control devices having specific components and structures are described and illustrated herein, it is to be understood that any selected embodiment can include one or more of the specific components and/or structures described for another embodiment where possible.

What is claimed is:

1. A pest control device, comprising:
   a bait adapted to be consumed or displaced by at least one species of termites; and
   a housing at least partially enclosing said bait;
   wherein said bait includes an extruded composite material that is palatable to termites; and
   wherein said composite material includes from about 5% to about 50% by weight of a plastic structural matrix comprising cellulose acetate butyrate; from about 50% to about 85% by weight of alpha cellulose contained within the matrix; and from about 0.001% to about 5% by weight of noviflumuron contained within the matrix.

* * * * *